US012811371B2

(12) United States Patent
Farzinpour

(10) Patent No.: US 12,811,371 B2
(45) Date of Patent: Nov. 24, 2026

(54) DEVICE FOR IONIZATION OF A FLUID

(71) Applicant: BRAIRTECH SWEDEN AB, Malmö (SE)

(72) Inventor: Behzad Farzinpour, Borås (SE)

(73) Assignee: BRAIRTECH SWEDEN AB, Malmö (SE)

( * ) Notice: Subject to any disclaimer, the term of this patent is extended or adjusted under 35 U.S.C. 154(b) by 0 days.

(21) Appl. No.: 18/861,912

(22) PCT Filed: May 2, 2023

(86) PCT No.: PCT/SE2023/050420
§ 371 (c)(1),
(2) Date: Oct. 31, 2024

(87) PCT Pub. No.: WO2023/214921
PCT Pub. Date: Nov. 9, 2023

(65) Prior Publication Data

US 2025/0149864 A1 May 8, 2025

(30) Foreign Application Priority Data

May 2, 2022 (SE) .................................... 2250531-7

(51) Int. Cl.
*H01T 19/04* (2006.01)
*A61L 9/18* (2006.01)
(Continued)

(52) U.S. Cl.
CPC ................ *H01T 19/04* (2013.01); *A61L 9/18* (2013.01); *A61L 9/22* (2013.01); *B01D 53/32* (2013.01);
(Continued)

(58) Field of Classification Search
None
See application file for complete search history.

(56) References Cited

U.S. PATENT DOCUMENTS

| | | | |
|---|---|---|---|
| 4,960,569 | A | 10/1990 | Fovell et al. |
| 6,451,208 | B1 | 9/2002 | Ledoux |

(Continued)

FOREIGN PATENT DOCUMENTS

| | | | |
|---|---|---|---|
| DE | 2606731 A1 | 8/1977 | |
| JP | H0761801 | 3/1995 | |
| WO | 2018211309 A1 | 11/2018 | |

OTHER PUBLICATIONS

International Search Report (Jun. 22, 2023) for corresponding International App. PCT/SE2023/050420.

(Continued)

*Primary Examiner* — Kenneth B Wells
(74) *Attorney, Agent, or Firm* — Muncy, Geissler, Olds & Lowe, P.C.

(57) ABSTRACT

A device for ionization of a fluid includes an elongated container adapted for conveying the fluid in a gaseous state, a fluid ionizing arrangement for ionizing the fluid, at least one fluid flow directing unit arranged in the container, wherein the at least one fluid flow directing unit includes at least one peripheral fluid flow guide channel having an outlet circumferentially displaced relative to an inlet for turning a first part of an incoming fluid flow, and a central fluid flow guide channel with an extension substantially in parallel with the longitudinal direction of the elongated container for guiding a second part of the incoming fluid flow substantially in the longitudinal direction of the elongated container.

21 Claims, 15 Drawing Sheets

(51) Int. Cl.

| | |
|---|---|
| ***A61L 9/22*** | (2006.01) |
| ***B01D 53/32*** | (2006.01) |
| ***C02F 1/46*** | (2023.01) |
| ***C02F 101/10*** | (2006.01) |

(52) U.S. Cl.

CPC ......... *C02F 1/4608* (2013.01); *A61L 2209/12* (2013.01); *A61L 2209/134* (2013.01); *B01D 2257/91* (2013.01); *B01D 2258/06* (2013.01); *B01D 2259/818* (2013.01); *C02F 2101/10* (2013.01); *C02F 2303/04* (2013.01)

(56) References Cited

U.S. PATENT DOCUMENTS

| | | | | |
|---|---|---|---|---|
| 9,390,894 | B2 | 7/2016 | Eden et al. | |
| 2002/0170817 | A1 | 11/2002 | Goudy, Jr. | |
| 2015/0174550 | A1 | 6/2015 | Tranquilla | |
| 2023/0126911 | A1* | 4/2023 | Uchitel | H05H 1/01<br>604/20 |

OTHER PUBLICATIONS

Buntat, Zokafle; Ozone generation using electrical discharges; A comparative study between Pulsed Streamer Discharge and Atmospheric Pressure Glow Discharge (2005).

* cited by examiner

DEVICE FOR IONIZATION OF A FLUID

BACKGROUND AND SUMMARY

The invention relates to a method for ionization of a fluid in a gaseous state.

Ionization is a process by which an atom or a molecule acquires a negative or positive charge by gaining or losing electrons, often in conjunction with other chemical changes. The resulting electrically charged atom or molecule is called an ion.

The technical field of the invention regards ionization of the fluid by subjecting the fluid to electrical discharges.

The fluid in gaseous state used as input to the ionization method may be air. When the electrical discharge is sufficiently strong, conditions are created for the gas to become separated into positive ions and electrons, wherein the air is ionized.

One area of application of an ionized gas is to clean a fluid, such as a gas, that may be air, or a liquid such as industrial process liquids and all kinds of water and wastewater and other liquids The ionized gas may be used for eliminating organic and mineral impurities or pollutants. Such organic matter may be bacteria, viruses, other harmful microorganisms, and some organic chemical substances. Another application of an ionized gas is separation by sedimentation of the inorganic or mineral substances such as metal.

The disclosure in this section should not be regarded as any admission of prior art.

WO2018/211309 discloses an electric arc ionization reactor and a method for generating ozone by using air. The reactor is elongated and has an inner circular cross section shape. An inlet for entry of air is provided at a first end of the elongated reactor and an outlet is provided at a second end of the elongated reactor. A pair of needle electrodes are arranged opposite each other and at a distance from each other in a transverse direction of the elongated reactor. An alternating current with high voltage is supplied to the electrodes for generating an arc between the electrodes.

Buntat, Zokafle; Ozone generation using electrical discharges; A comparative study between Pulsed Streamer Discharge and Atmospheric Pressure Glow Discharge (2005). This thesis deals with an investigation into atmospheric pressure glow discharge and pulsed streamer discharge techniques of ozone generation, in an attempt to compare their performances in the generation of a high concentration and high yield of ozone. The art includes the comparison of the different methods of utilization of the corona discharge in atmospheric pressure by use of dielectric plates with the distance of maximum 1 mm from each other.

US20020170817 discloses the generating of a corona or other electric discharge and provides for the passing of a gas through the corona to effect ionizing, creating of ozone or the like. According to various methods of the invention, a corona discharge (or other electric discharge) is created, a gas is passed through the corona discharge; mixing of the gas may be provided by a motionless mixing technique for one or more purposes, and such as to assure maximum exposure of the gas to the corona discharge, to provide uniform temperature of the gas, to cool the corona generator, etc.

JP0761801 discloses an ozonizing unit providing a high ozone concentration by connecting a high-frequency power source across prescribed electrodes, carrying out the corona discharge and regulating the electric current while making the produced ozone gas flow in a spiral form and preventing ozone from being destroyed.

U.S. Pat. No. 4,960,569A discloses a corona discharge ozonator that comprises a first electrode, a second electrode and a dielectric material disposed between the electrodes. An ozonization chamber is formed between one of the electrodes and the dielectric material and defines a fluid flow path. A plurality of thermally-conducting solids are within the fluid flow path.

U.S. Pat. No. 6,451,208 discloses a device for applying electrostatic and magnetic fields to a fluid which includes an outer conduit and an inner conduit forming a fluid passageway therebetween. The inner conduit is connected to a DC power source and the outer conduit along with electrode needles in electrical communication therewith are connected to ground. A baffle is positioned within the passageway to impart a spiral motion to the fluid flowing therein.

It is desirable to provide a device for ionizing a fluid flow, which creates conditions for a high ionization efficiency.

According to an aspect of the invention, a device for ionization of a fluid is provided, wherein the device comprises an elongated container adapted for conveying the fluid in a gaseous state, a fluid ionizing arrangement for ionizing the fluid, at least one fluid flow directing unit arranged in the container, wherein the fluid flow directing unit comprises at least one peripheral fluid flow guide channel having an outlet circumferentially displaced relative to an inlet for turning a first part of an incoming fluid flow, and a central fluid flow guide channel to an extension substantially in parallel with the longitudinal direction of the elongated container for guiding a second part of the incoming fluid flow substantially in the longitudinal direction of the elongated container.

The at least one peripheral fluid flow guide channel and the central fluid flow guide channel create conditions for directing the first part of the fluid flow and the second part of the fluid flow in different directions. According to one example, it may be used for directing the different parts of the fluid flow to different outlets (for different purposes). According to a further example, one fluid flow part may be directed to a first outlet that is in communication with a certain application (for example a tank for cleaning a liquid) and another part of the fluid flow part may be directed to an inlet of the container for recirculation of that part of the fluid flow.

The at least one peripheral fluid flow guide channel creates conditions for directing the first part of the fluid flow in a helical path. Such a fluid flow pattern allows the fluid to spend more time in the container, which creates conditions for increasing the combination rate and the likelihood of collisions and therefore an ionization rate which leads to a higher ionization efficiency. Further, in case the fluid ionizing arrangement comprises electric means for creating an arc structure, such a flow pattern may cause the fluid flow to arrive at the arc structure with a direction angled in relation to a longitudinal direction of the container which in turn may cause more molecules to be ionized by the arc structure. Further, such a flow pattern may cause turbulence in the fluid flow, which in turn may cause more molecules to be ionized by the fluid ionizing arrangement.

The central fluid flow guide channel creates conditions for directing the second part of the fluid flow along a substantially straight path inside of the container. In case the fluid ionizing arrangement comprises electric means for creating an arc structure and the first fluid flow directing unit is arranged upstream of the electrodes, such a flow pattern may be directed to a desired position relative to the electrodes, such as towards a position between the electrodes. The second portion of the fluid may in this way contribute substantially to push an arc structure downstream and thereby create conditions for a high coverage of the cross section of the container and thereby a high ionization efficiency.

According to one example, the fluid flow directing unit is rotationally rigidly connected to the container. It may be achieved via weld seams. It creates conditions for maintaining the first fluid flow directing unit in its desired operational position in the container during operation of the device.

According to one embodiment example, the fluid flow directing unit comprises a plurality of circumferentially spaced peripheral fluid flow guide channels. It creates conditions for a more uniform distribution of the fluid flow downstream of the first fluid flow directing unit.

According to a further embodiment example, the at least one peripheral fluid flow guide channel has a substantially larger dimension than the central fluid flow guide channel for conveying a substantially larger part of the incoming fluid flow. It may be beneficial in an application as mentioned above, where the central straight flow is used to deflect an arc structure downstream, wherein only a smaller amount of a total fluid flow may be required for affecting the deflection of the arc structure.

According to a further embodiment example, the container has a rounded inner surface and the fluid flow directing unit has a rounded peripheral surface substantially corresponding to a curvature of the rounded inner surface of the container, wherein the fluid flow directing unit is arranged in the container so that the rounded surfaces are in contact with each other. It creates conditions for creating a fluid tight connection between the facing surfaces of the container and the fluid flow directing unit. In other words, it creates conditions for minimizing leakage of fluid past the fluid flow directing unit.

According to a further embodiment example, the fluid flow directing unit comprises a body defining the at least one peripheral fluid flow guide channel and the central fluid flow guide channel. It creates conditions for a cost-efficient production. According to one example, the fluid flow directing unit comprises a single body defining the at least one peripheral fluid flow guide channel and the central fluid flow guide channel.

According to a further embodiment example, an inner surface of the elongated fluid container has a circular shape in a cross section transverse to its longitudinal direction and a radially outer surface of the fluid flow directing unit defines a circular shape of substantially the same dimension as the inner surface of the elongated fluid container. It creates conditions for creating a fluid tight connection between the facing surfaces of the container and the fluid flow directing unit.

According to a further embodiment example, the inner surface of the elongated fluid container has a diameter in a range of 10-50 mm, especially in the range of 10-30 mm and preferably in the range of 15-25 mm. It has been determined that a container of such a dimension creates conditions for a high ionization efficiency with a relatively cost-efficient operation and/or long life of the ionization device.

According to a further embodiment example, the device comprises a first fluid flow directing unit and a second fluid flow directing unit adapted for directing at least a part of the fluid flow in a helical path inside of the container and wherein the first fluid flow directing unit is arranged spaced from the second fluid flow directing unit downstream in the longitudinal direction of the container and arranged so that the at least one peripheral fluid flow guide channel deflects the fluid flow from the helical path.

The downstream fluid flow directing unit may be adapted to compensate for a pressure drop throughout the length of the container by providing a hindrance to the fluid flow. More specifically, the pressure in the container may be maintained or at least not significantly reduced due to the fluid flow directing unit. Further, a distance between the molecules is decreased and the retention time in the container is increased and consequently the ionization efficiency increases. Further, maintaining the pressure at a relatively high level may be important for the delivery of the fluid to a downstream application, such as a tank comprising a liquid for purification, since the liquid in the tank provides a counterpressure that needs to be overcome.

Further, the ionization device may comprise two pairs of electrodes that are spaced in a longitudinal direction of the container. By arranging the fluid flow directing units on opposite sides of the two pairs of electrodes in the longitudinal direction of the container, a second arc structure created by the second, downstream, pair of electrodes may be as strong and disciplined as the first arc structure created by the first pair of electrodes.

According to a further embodiment example, the fluid ionizing arrangement comprises a first pair of electrodes arranged in the elongated container opposite each other and at a distance from each other in a transverse direction of the elongated container, wherein the container is adapted for conveying the fluid in a fluid flow past the first pair of electrodes, wherein the device further comprises a power supply adapted to charge the first pair of electrodes so that discharges take place from the electrodes. Ionization of a fluid by means of electrically created arcs creates conditions for a high ionization efficiency.

According to a further embodiment example, the second fluid flow directing unit is arranged in the container upstream of the first pair of electrodes in a direction of the fluid flow, wherein the central fluid flow guide channel is adapted for guiding the second part of the incoming fluid flow towards a position between the electrodes in the first pair for deflecting the first arc structure downstream.

According to a further embodiment example, the first fluid flow directing unit is arranged in the container downstream of the first pair of electrodes in a direction of the fluid flow.

According to a further embodiment example, the power supply is adapted to charge the first pair of electrodes so that they are simultaneously negatively or positively charged for creating such a potential difference between each one of the electrodes and an environment of the respective electrode that electric discharges takes place from each one of the electrodes, wherein the container is adapted for conveying the fluid in a gaseous state in a flow past the first pair of electrodes in the environment of the respective electrode during said charging for ionization of the fluid.

More specifically, both electrodes exchange electrons/positrons with the environment of the respective electrode, eventually leading to a discharge and creation of independent semi arc structures in the vicinity of the respective electrode, in interaction with the conveyed fluid. The term “semi” here means that the arcs extend from the respective electrode a distance into the container, but there are no continuous arcs extending between the electrodes in the first pair.

According to a further embodiment example, the device comprises a second pair of electrodes arranged in the container opposite each other and at a distance from each other, wherein the second pair of electrodes are arranged at a distance from the first pair of electrodes downstream of the first pair in a fluid flow direction in the container, wherein the power supply is adapted to charge each one of the electrodes in the second pair of electrodes so that they are simultaneously negatively or positively charged and to synchronize the charging of the first pair of electrodes in relation to the second pair of electrodes so that the second pair of electrodes are negatively charged when the first pair of electrodes are positively charged and vice versa.

According to a further embodiment example, a first electrode in the first pair of electrodes and a first electrode in the second pair of electrodes are connected to opposite terminals of a first power supply and wherein a second electrode in the first pair of electrodes and a second electrode in the second pair of electrodes are connected to opposite terminals of a second power supply.

The method creates conditions for creating a configuration of first independent semi arc structures that are especially effective in ionization of the fluid. It may be achieved by supplying the voltage of a certain magnitude to the first pair of electrodes so that both electrodes simultaneously are of the same charge at each moment and providing the fluid in a fluid flow rate matching the magnitude of the voltage. More specifically, the method creates conditions for creating a configuration of the first arc structure downstream of the electrodes that covers a cross section of the container to a large extent and more specifically may cover a space in the shape of a hemisphere, which in turn creates conditions for ionization of the fluid passing the first arc structure to a large extent. The first arc structure created may comprise a specific type of arcs, that may be called "Ario-arcs" or "Ario discharge" (Arc-Rotary-Ionization-Orbitals), having certain characteristics, such as a plurality of arcs, permanency of the arcs and stability of the arcs.

In other words, the first arc structure may be configured to cover a substantial part of the container in a cross section so that when a stream of atoms/molecules in the fluid flow is conveyed past the electrodes, it makes it difficult for the atoms to pass without getting ionized.

According to one example, the discharges from the electrodes form "half-arcs" affecting substances passing through the space between the two electrodes.

According to a further example, at least one arc at a time in the first arc structure is permanent and continuous.

According to one example, the first arc structure comprises an arc having a zigzag shape like saw teeth due to the fact that the electrons push each other away due to the same electric charge. In the tips of the saw shaped arc parts, the ionization energy availability is higher (ionization happens relatively easier there) because the electrons are more excited there.

The wording "emit" electrons from the electrodes may alternatively be termed "discharge" electrons.

The method may be used for production of ROS (reactive oxygen species) and some other substances. The fluid used may here be air. After ionization, the fluid comprises a mixture of ROS (reactive oxygen species), such as Oxygen ($O_2$), Superoxide anion ($O_2^-$), Peroxide ($O_2^{-2}$), Hydrogen Peroxide ($H_2O_2$), Hydroxyl radical (OH) with Hydroxyl ion ($OH^-$). This is a homogenous mixture of the ROS, and the mixture is substantially stable and radicals that have a relatively higher half-life. It may be maintained stable to be used in a downstream application, such as a tank for cleaning of an industrial process fluid. According to one example, the process fluid is a cutting fluid resulting from an industrial cutting operation.

According to one example, the method comprises the step of supplying a magnitude of the voltage to the first pair of electrodes so that selective ionization is achieved. For example, oxygen ionizes at a lower energy than nitrogen. More specifically, an ionization energy of about 1400 KJ/mol would ionize oxygen and not nitrogen. The ionization energy is carefully controlled for a specific application for preferably ionizing all the elements to oxygen and not nitrogen and more atomic numbers, to avoid producing NOx ($NO_3$-$HNO_3$) and subsequently odor. The voltage range supplied to the electrodes is chosen in a way that the available energy for the ionization of the gaseous elements is high enough to ionize oxygen but not high enough to ionize the nitrogen.

Even in a long-term use of the device and depreciation of the power source (such as a transformer) the power would still end up below the energy level for ionizing the nitrogen, and therefore, the undesired by-products are still avoided. This is one benefit of this art and is what distinguishes it from many prior arts ranging from UV and Ozone generators, which ionize nitrogen (first ionization) and oxygen (second ionization) and therefore produce the mentioned undesired by-products. For example, as the UV lamp depreciates, the wavelength of the emitted electromagnetic wave alters and that alteration, affect the availability of the ionization energy.

According to one example, the electrodes in the first pair of electrodes are straight and of a rod-type with a pointy end (like a needle) and arranged in-line with each other.

According to a further embodiment example, the device comprises a magnetic field generating arrangement, which is adapted for generating a magnetic field in the vicinity of the first pair of electrodes for affecting the arc structure for supporting the ionization of the fluid.

According to one example, the magnetic field generating arrangement is arranged outside of the container. It creates conditions for a longer life since the magnetic field generating arrangement may be arranged in an environment less aggressive than the environment in the container.

According to one example, the magnetic field generating arrangement comprises a first section arranged upstream of the first pair of electrodes in the longitudinal direction of the container, wherein the first arc structure comprises a first set of arcs that are deflected downstream from the electrodes by the fluid flow and a second set of arcs extending upstream from the electrodes by the effect of the magnetic field of the first magnetic field generating section.

According to one example, which may be used as a complement or alternative to the last-mentioned example, the magnetic field generating arrangement comprises a second section, which is arranged downstream of the first pair of electrodes in the longitudinal direction of the container, wherein the second magnetic field generating section is adapted for generating a magnetic field in the vicinity of the first pair of electrodes for stabilizing the first arc structure.

Arranging the magnetic field in a proper way creates conditions for creation of a plurality of the semi-arcs spreading and increasing the coverage of the cross section of the container, increasing the probability of effective ionization of the conveyed fluid depending on the flow rate of the fluid and the cross section area of the container.

The term "semi arc" structure may be regarded as an arc structure between the prior art arc structures of glow corona and streamer corona. However, since the semi arc structure introduced by this art does not have a ground pole and/or dielectric, it does not fall within the category of corona discharge and therefore it has a specific shape by a specific arrangement of magnetic field (but according to the vision error it may look like a complete arc extending between the electrodes).

According to a further embodiment example, the device comprises a fluid flow pumping means for supplying the fluid flow to an inlet of the container with a fluid flow rate in a range of 5-80 litre/min, especially 5-40 litre/min and preferably 8-20 litre/min. One aspect of the embodiment example is to deflect an arc structure by means of the fluid flow. For achieving such an arc structure deflection, the fluid flow rate is preferably in the above mentioned range for this application and especially matched with other parameter ranges. It creates conditions for an arc structure that has the following features: a high number of semi arcs, high geographical/spatial coverage of semi arcs in the vicinity of each electrode environment per cross section of the container and an increase in ionization probability (exposure of fluid to semi arc) and ionization efficiency as a result.

According to a further embodiment example, the device comprises a fluid flow pumping means that is adapted for supplying the fluid flow in a pulsed manner to the inlet of the container.

One effect of the pulsing is that there will be pressure fluctuations inside the container that leads to a "hammer-drill-effect", wherein a distance between the molecules is decreased (and thereby a higher likelihood of ionization). Further, the pulsing causes the arcs to have greater thickness compared to as if there were no pulsing. Thus, the pulsing creates conditions for a higher ionization efficiency.

A further effect of the pulsing is that for generating the same yield of oxidants, a lower volume of air is required as feed to the container, which provides for cost efficiency.

According to a further embodiment example, the electrodes in the first pair of electrodes are arranged at a distance from each other in a range of 2-15 mm, especially for a range of 2-10 mm and preferably in a range of 2-4 mm.

According to one example, for a container with a diameter in the range 15-25 mm, the distance between the electrodes is in the range of 2-4 mm. In this way, corrosion is minimized and the lifespan of the device is thereby increased and/or it may be more cost-effective in use in low maintenance by substituting the electrodes with new ones less frequently. According to an alternative or complement, the electrodes are provided with chemical coatings with materials such as nano-Titanium dioxide or nano-platinum or any other material that increases the corrosion resistance of the electrodes.

According to a further embodiment example, each one of the electrodes in the first pair has an elongated shape with a pointy end and wherein the electrodes are arranged so that the pointy ends face each other. According to one example, the electrodes in the first pair of electrodes are arranged so that their longitudinal directions are in parallel to each other and preferably in-line with each other.

According to a further embodiment example, each one of the electrodes in the first pair has an elongated shape with a pointy end defining an angle in a range of 20-35°. Such sharp tips of the electrodes creates conditions for creating several paths of electrons emitted from the angled surface of the electrode at longitudinally spaced locations. According to one example, the electrodes in the first pair of electrodes are identical.

According to a further embodiment example, the method comprises the step of supplying such a voltage to the first pair of electrodes that both electrodes have either positive or negative charge simultaneously.

Consequently, at a certain point in time, both electrodes in the first pair of electrodes are positively charged and therefore emit electrons, wherein the fluid flow in the environment of the respective electrode may be regarded to form a negatively charged region for interaction with the emitted electrons from the electrodes so that a first arc structure is created projecting from each one of the electrodes for ionization of the fluid.

According to a further embodiment example, the method comprises the step of supplying the voltage to each electrode in the first pair of electrodes in a range of 2-15 kV, especially in a range of 5-10 kV and preferably around 7.5 kV. It has turned out that a maximum energy level of about 1500 KJ/mol may be achieved with 7.5 kV per electrode for enabling the selective ionization as defined above.

According to one example, a transformer is connected to both electrodes in the first pair for supplying the voltage. According to one example, AC power from a power source, such as the grid, goes to the transformer. Then the transformer converts the voltage from 240V to 2*7.5 kV for each pole (associated to one of the electrodes) by changing the electric charge of the electrodes (AC current).

According to one example, a transformer is connected with one of its output terminals to a first electrode in the first pair (and possibly with another one of its terminals to a first electrode in the second pair) for supplying the voltage. According to one example, AC power from a power source, such as the grid, goes to the transformer. Then the transformer converts the voltage from an input of 12 to 220 volts with a frequency of 50 to 60 Hz to 2*7.5 kV for each pole (associated to one of the electrodes) with a frequency of about 20 kHz by changing the electric charge of the electrodes (AC current).

According to one example, supplying power to the electrodes with high frequency and high voltage creates conditions for causing a permanent and continuous arc which is strong enough not to be adversely affected by the passing fluid flow (up to 80 litres per minute). The higher frequency (of transformer) from 10, the greater number of arcs are shaped and seen.

According to a further embodiment example, the device is adapted to be operated with a pressure in the container above 1.1 bars.

According to a preferred example, the device is adapted to be operated with a pressure in the container above 1.5 bars. According to one example, it may be operated with a pressure in the container in a range of 1.5-2.0 bar. A pressure level above 1.1 bars increases the likelihood of more collisions of matter and therefore a higher ionization efficiency. The pressure required in the container is further dependent on a downstream application, wherein the pressure level may be up to 10 bars.

Accordingly, the pressure in the container is greater than the atmospheric pressure during the charging of the electrodes, wherein an increased pressure in a given volume in the vicinity of each electrode leads to higher chance of collision and ionization around the respective electrode.

According to a further embodiment example, the device comprises a light source arranged for radiating the fluid in the container. The light-matter interaction provides for the phenomenon of pair production. In the area in which the arcs are formed, the interaction between the photons from the light source with the substances passing by the area, leads to emission of waves with different ranges of wavelength depending on the light source. The generated waves enhance the ionization efficiency. Additionally, electrons and positrons are released, and they contribute to the ionization reactions. And the yield per power consumption is increased.

The light source is preferably arranged outside of the container. It creates conditions for a long life of the light source since it will not be subjected to the interior environment (friction and heat) of the container. The radiation by the light source may radiate the fluid flow provided the container wall is transparent, such as made of glass.

The light source may be light-emitting diodes (LED) adapted for radiating an ultraviolet (UV) light. According to an alternative, a Xenon lamp may be used. According to one example, the light sources may be adapted to provide a light intensity in a range of 100-5600 Lumen. The light intensity may be matched to the magnitude of the voltage supplied to the electrodes, wherein a lower voltage may be compensated by a higher light intensity for a certain ionization effect.

The light source may contribute to a significantly increased ionization efficiency. Tests have shown results of an increased ionization efficiency of up to 40%.

According to a further example, the ionization device comprises a second pair of electrodes arranged in the container at a distance from the first pair of electrodes. According to one example the distance between the adjacent electrode pairs is at least 30 mm.

Further advantages and advantageous features of the invention are disclosed in the following description claims.

BRIEF DESCRIPTION OF THE DRAWINGS

With reference to the appended drawings, below follows a more detailed description of embodiments of the invention cited as examples.

In the drawings.

DETAILED DESCRIPTION OF EXAMPLE EMBODIMENTS

Figure 1:
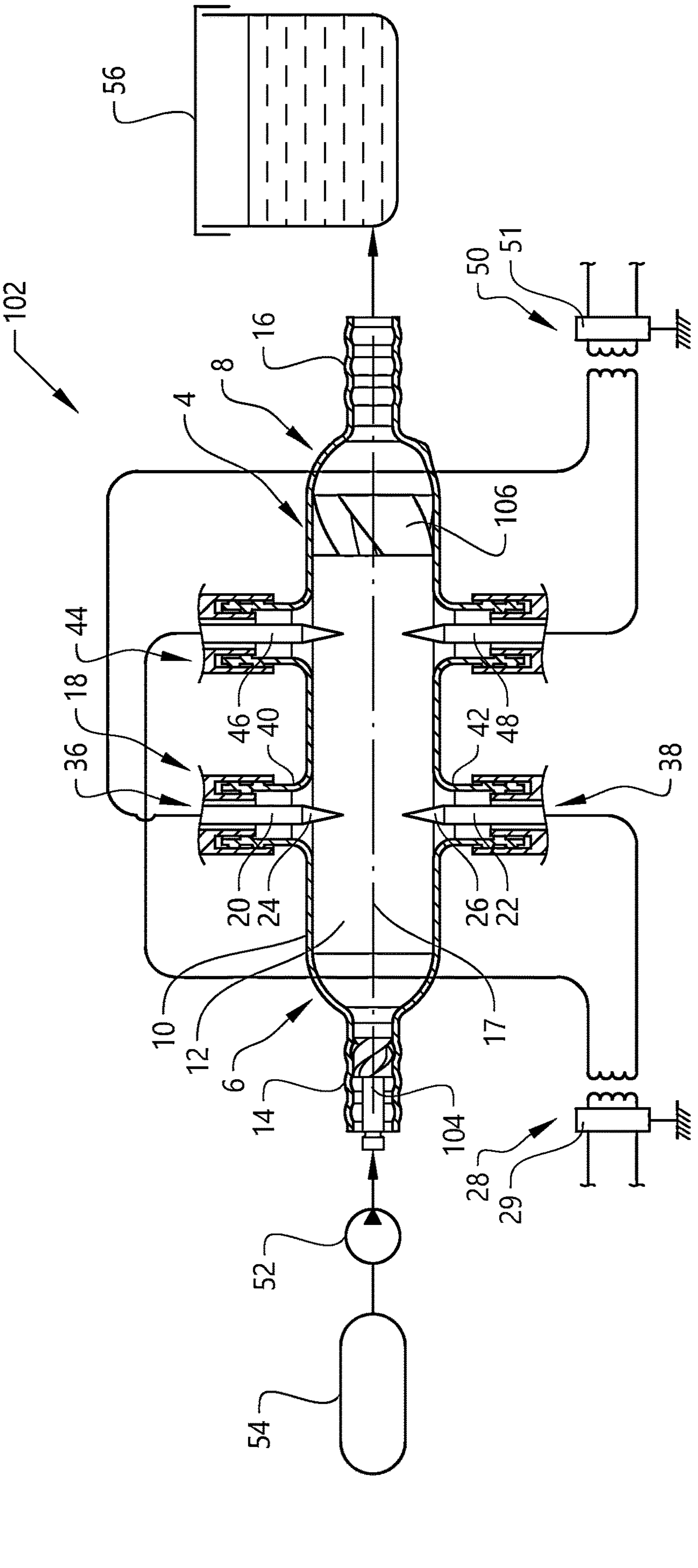
FIG. 1 is a schematic view of a device for ionization of a fluid according to a first embodiment, wherein a container is shown in a cross section.
Figure 2:
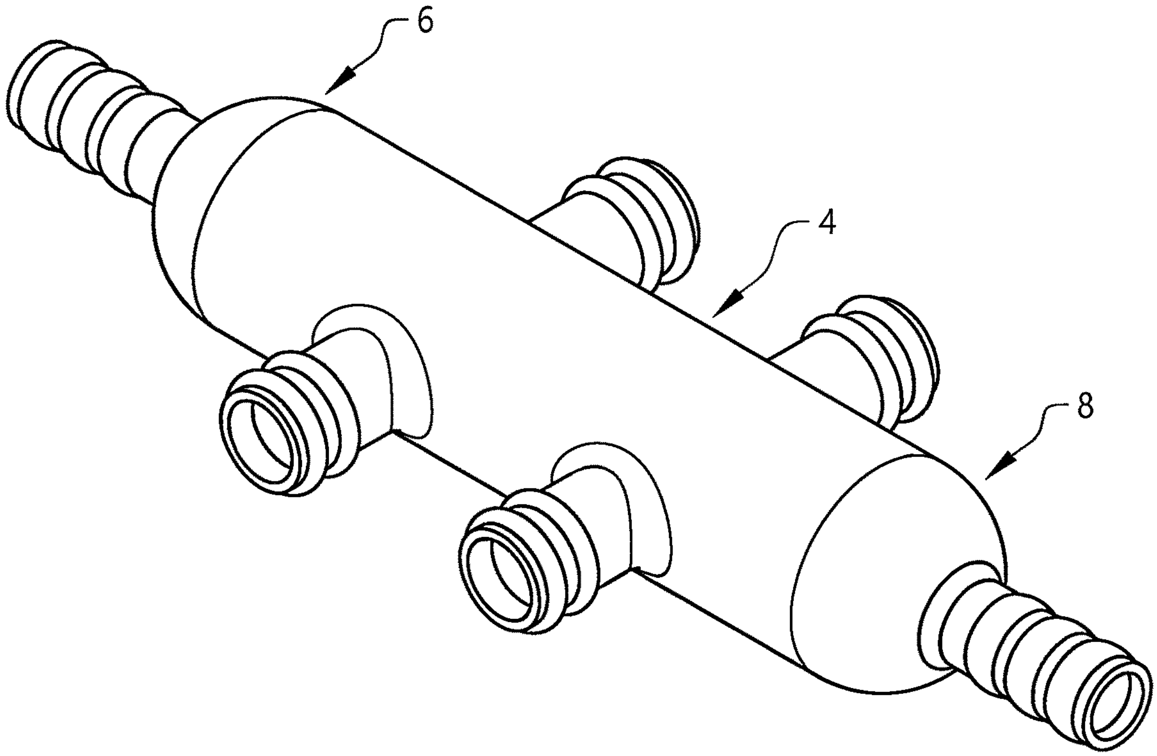
FIG. 2 is a perspective view of the container in FIG. 1.

FIG. 1 is a schematic view of a device 102 for ionization of a fluid in a gaseous state according to a first embodiment. The fluid in gaseous state will in the following be referred to as a gas. According to one example, the gas is air. The ionization device 102 comprises a container 4. The container 4 is illustrated in a cross section in a horizontal plane through its center axis. The container 4 has an elongated shape. The container 4 has a rounded cross section shape and more specifically a circular cross section shape. Further, the cross section of the container 4 is constant along a significant portion of the length of the container. Further, ends 6, 8 of the container 4 in the longitudinal direction have a rounded and more specifically half-spherical shape. A wall 10 of the container 4 defines an inner chamber 12. An inner surface of the wall 10 of the elongated container 4 has a diameter of about 20 mm. FIG. 2 is a perspective view from above the container 4 in FIG. 1.

The container wall 10 is formed of glass. The container may be formed in two identical container parts with a delimitation in a plane through a center axis of the container 4. According to an alternative, the container 4 is formed in one-piece with a cap at one end.

Further, an inlet 14 is provided at a first end 6 of the container 4 in its longitudinal direction and an outlet 16 is provided at a second end 8 of the container 4 in its longitudinal direction for conveying a gas flow from the inlet 14 to the outlet 16. Each one of the inlet 14 and the outlet 16 has a generally tube shape. An axis of the inlet 14 has a main direction in parallel with the longitudinal direction of the container 4 and is arranged in-line to a longitudinal center axis 17 of the container. Likewise, an axis of the outlet 16 has a main direction in parallel with the longitudinal direction of the container 4 and is arranged in-line to the longitudinal center axis 17 of the container. The container 4 has a length in a range of 100-120 mm excluding the inlet 14 and outlet 16.

Figure 3:
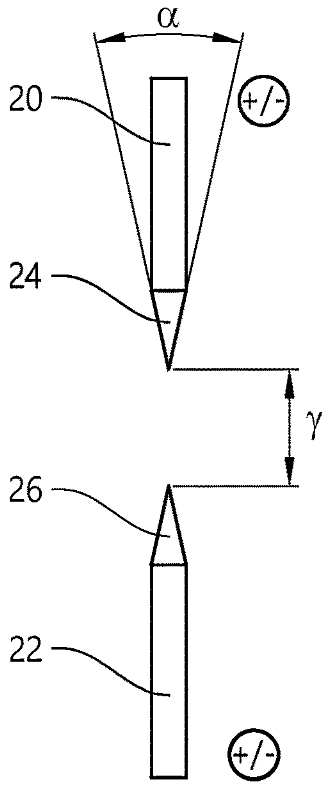
FIG. 3 is an enlarged view of a first pair of electrodes in FIG. 1.

The ionization device 102 further comprises a first pair 18 of electrodes 20, 22 arranged in the container 4 opposite each other and at a distance from each other. The electrodes 20, 22 are arranged perpendicularly relative to the longitudinal direction of the container 4. Further, the container 4 is arranged in a way that its longitudinal direction is in a horizontal plane. More specifically, the electrodes 20, 22 are arranged so that they extend in a horizontal plane. The electrodes 20, 22 are shown in an enlarged view in FIG. 3. The electrodes 20, 22 are arranged at a distance y from each other in a range of 2-4 mm. Further, each one of the electrodes 20, 22 in the first pair 18 has an elongated shape with a circular cross section and a pointy end 24, 26. The electrodes are arranged so that the pointy ends 24, 26 face each other. More specifically, each one of the electrodes 20, 22 in the first pair 18 has an elongated shape with a pointy end 24, 26 defining an angle α in a range of 20-35°. In other words, each one of the electrodes 20, 22 has a sharp tip. More specifically, the electrodes 20, 22 in the first pair 18 are straight and arranged in-line with each other. More specifically, the electrodes 20, 22 in the first pair 18 are in the form of rods. The electrodes 20, 22 in the first pair 18 may be termed needle electrodes. The electrodes 20, 22 in the first pair 18 are formed in a metallic material and more precisely of tungsten (also called wolfram) as an example.

According to physics law, when charging an element, the charged parts accumulate in any sharp edges of the element. Accordingly, charged parts will be highly accumulated in the sharp edge of the electrode, 20, 22. In other words, charged parts will have a very high density in the sharp edge, wherein an electric field will be strong in a region of the sharp edge. Further, a highly charged electrode (positive or negative) will have a very high potential in relation to the environment (adjacent the electrode). The potential difference between the electrode and its adjacent environment/surroundings will result in ionization of the matter in the environment in the vicinity of the respective electrode leading to exchange of electrons/positrons in cycles from higher potential area to lower potential area and vice versa and different types of electric discharge from the electrode may take place. This phenomenon may be similar to a Tesla coil. Accordingly, the design of the electrodes 20, 22 with sharp tips 24, 26 creates good conditions for creating electric discharges in the form of electric arcs from the surface of the tip having an inclination relative to the longitudinal direction of the elongate electrode. More specifically, a first set of arcs may be created extending from the electrode tip in a downstream direction. Further, a second set of arcs may be created extending from the electrode tip in an upstream direction. It will be described in more detail below in association with FIG. 14 and FIG. 15.

The ionization device 102 further comprises a power supply 28 adapted to for charging each one of the electrodes 20, 22 in the first pair 18 of electrodes so that they have the same charge simultaneously. In this way, such a potential difference between each one of the electrodes 20, 22 and an environment of the respective electrode may be created that electric discharges take place simultaneously from each one of the electrodes. Further, the fluid is conveyed in a gaseous state inside the container past the first pair 18 of electrodes in the environment of the respective electrode 20, 22 during said charging for ionization of the fluid.

More specifically, the power supply 28, 50 comprises two transformers 28, 50, which are adapted to provide an alternating current of a certain frequency to the electrodes. Accordingly, the power supply 28, 50 is adapted supply such a voltage to the first pair 18 of electrodes that both electrodes 20, 22 are positively charged at the same time and therefore emit electrons. It is schematically shown in a top view in FIG. 4, wherein the arrows 30, 31 indicate paths of electrons emitted from the tips of the electrodes 20, 22. Further, the container 4 is adapted for conveying the gas in a flow past the first pair 18 of electrodes, wherein the gas flow may be regarded as a negatively charged region 32 between the electrodes 20, 22 for interaction with the emitted electrons from the electrodes so that a first arc structure 34 may be created. More specifically, a plurality of electric arcs project from each one of the electrodes 20, 22 for ionization of the gas. FIG. 5 is a schematic front view of the first arc structure 34 created in the container according to FIG. 4. Further, each arc has a zigzag shape in the form of saw teeth.

More specifically, each transformer 28, 50 comprises a primary winding and a secondary winding. Each transformer converts the voltage from an input of 12 to 220 volts with a frequency of 50 to 60 Hz to 2*7.5 kV for each pole (associated to one of the electrodes) with a frequency of about 20 kHz by changing the electric charge of the electrodes (AC current). Accordingly, each transformer 28, 50 comprises a frequency converter 29, 51 where one of the ground wire functions is to reduce noise.

Figure 4:
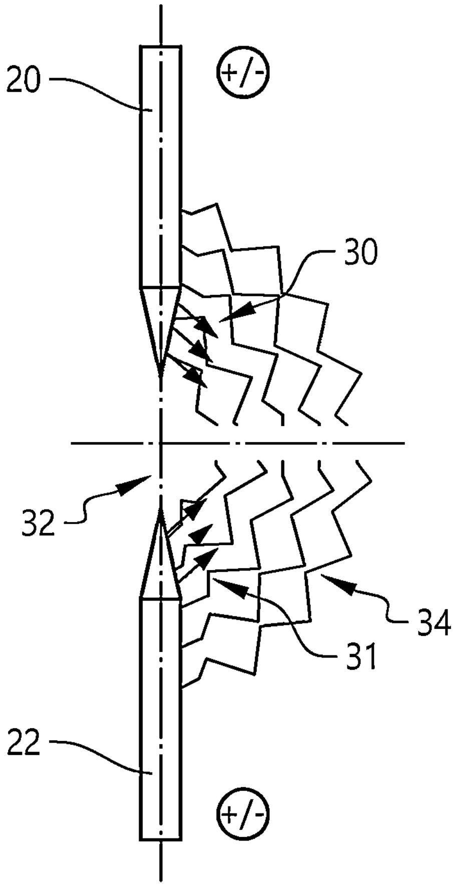
FIG. 4 is a schematic top view of a first arc structure created in the container according to FIG. 1 by the first pair of electrodes.
Figure 5:
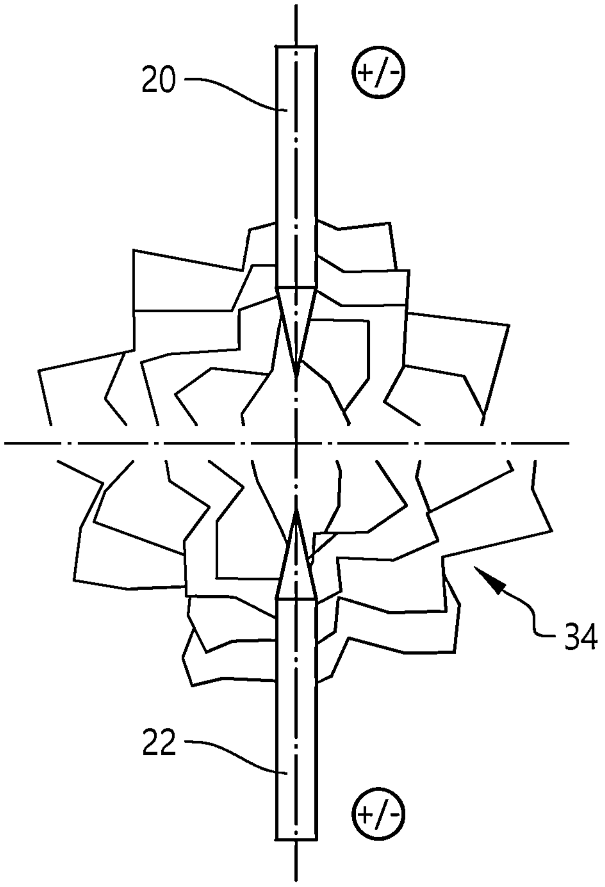
FIG. 5 is a schematic front view of the first arc structure created in the container according to FIG. 1 by the first pair of electrodes.

It should be noted that the zigzag arc shapes shown in FIG. 4 and fig . . . 5, are only schematically shown. Especially, the semi-arcs are magnified and much bigger than the real size in relation to the size of the electrodes 20, 22. In reality the zigzags are in microscopic scales. Also, their plurality is much higher than the number of the arcs shown in the figures.

Each one of the transformers 28, 50 is adapted for supplying an output voltage at a magnitude of around 7.5 kV via each one of its output terminals. Further, each one of the transformers 28, 50 is adapted for supplying the output voltage in a frequency about 20 kHz, wherein the polarity of the electrodes connected to the two output terminals/poles of one transformer will change very fast (every 0.00005 second).

More specifically, each one of the electrodes 20, 22 is arranged in an opening 36, 38 through the container wall 10. More specifically, the container comprises a pipe-shaped portions 40, 42 extend in a transverse direction relative to the longitudinal direction of the container 4. More specifically, the pipe-shaped portion 40, 42 extends perpendicularly relative to the longitudinal direction of the container 4. The pipe-shaped portions 40, 42 define the openings 36, 38. More specifically, the pipe-shaped portions 40, 42 are formed in one-piece with the container 4. More specifically, the electrodes 20, 22 are arranged in the pipe-shaped portions 40, 42 in a gas tight manner for avoiding leakage.

The ionization device 102 further comprises a second pair 44 of electrodes 46, 48 arranged in the container 4 in a similar way as has been described above with regard to the first pair 18 of electrodes 20, 22. The second pair 44 of electrodes 46, 48 are arranged at a distance from the first pair 18 of electrodes 20, 22 in the longitudinal direction of the container 4. Each one of the first pair 18 of electrodes 20, 22 and the second pair 44 of electrodes 46, 48 are arranged at the portion of the container 4 having a constant cross section with a distance between the adjacent electrode pairs of about 30 mm.

The power supply 28, 50 is adapted for charging each one of the electrodes 46, 48 in the second pair 44 of electrodes so that they have the same charge at the same time. In this way, such a potential difference between each one of the electrodes 46, 48 and an environment of the respective electrode may be created that electric discharges take place from each one of the electrodes separately. Accordingly, the power supply 28, 50 is adapted to supply such a voltage also to the second pair 44 of electrodes that both electrodes 46, 48 are positively charged at the same time and therefore emit/exchange electrons/positrons.

The arrangement is adapted to synchronize the charging of the first pair 18 of electrodes 20, 22 in relation to the second pair 44 of electrodes 46, 48 so that the second pair 44 of electrodes 46, 48 are negatively charged when the first pair 18 of electrodes 20, 22 are positively charged and vice versa.

The two transformers 28, 50 are of the same natural frequency and identical. By arranging the transformers 28, 50 adjacent each other in relative close proximity, their frequency cycles will become synced eventually in a steady state since they would influence each other during operation, due to Hertz and frequency laws. Accordingly, they can work with a synced frequency permanently. Accordingly, this synchronization happens spontaneously as soon as the transformers are turned on. According to an alternative, means may be provided to actively control the synchronization, such as arranging a one-way diode (a diode that synchronizes the direction of the current in the same direction—the sine or cosine wave) in the path of each exit terminal.

Accordingly, each one of the transformers has two output terminals/poles, which are connected to the electrodes 20, 22; 46, 48 for charging the electrodes. When the potential reaches an amount that is sufficient for electric discharge, the above-mentioned phenomenon of electric discharge will take place. More specifically, a first electrode 22 in the first pair 18 of electrodes and a first electrode 46 in the second pair 44 of electrodes are connected to opposite terminals of the first transformer 28. Further, a second electrode 20 in the first pair 18 of electrodes and a second electrode 48 in the second pair 44 of electrodes are connected to opposite terminals of the second transformer 50.

The ionization device 102 further comprises a gas flow pumping means 52 for supplying the gas flow from a tank 54 of compressed air to the inlet 14 of the container 4. More specifically, the gas flow pumping means 52 is adapted for supplying the gas flow at such a rate to the container 4 that it is conveyed past the first pair 18 of electrodes 20, 22 so that at least parts of the first arc structure are deflected downstream from the electrodes 20, 22 in a direction of the gas flow. More specifically, the gas flow pumping means 52 is adapted for supplying the gas flow to the container with a gas flow rate in a range of 10-12 litre/min.

It may be noted that the device is not limited to an application of a tank for supply of the gas. It can alternatively be a compressor using ambient air or an industrial blower, etc.

Further, the gas flow pumping means 52 is adapted for supplying the gas flow to the inlet 14 of the container 4 in a pulsed manner. The method comprises the step of supplying the gas flow in a pulsed manner to the inlet 14 of the container 4 via a pulsing duration at about 0.5 seconds with a pause between consecutive pulses of about 1.5 seconds, see the graph in FIG. 21.

The outlet 16 of the container 4 is in fluid communication with a tank 56 comprising a process liquid, such as industrial water or wastewater that have strong aerobic or anaerobic bacteria. A line connecting the outlet 16 with the tank 56 ends in a lower region of the tank 56 so that the ionized gas may be supplied below a surface of the process liquid in order to separate inorganic or mineral substances such as metal by sedimentation or kill the bacteria.

According to an alternative, the tank 56 is replaced with another device that relates to air purification. The ionized gas exiting the outlet can be directly sprayed to a room to eliminate virus, bacteria, odour, etc.

A further effect of the pulsing is that a lower amount of unionized air (O2) per volume of output is sent to the tank 56. Unionized air may risk support the aerobic bacteria to grow and it will compete to the ionized portion of the air. With pulsing, more ionized air compared to unprocessed air (O2) is sent in the mixture per volume of output fluid.

The ionization device 102 further comprises a nozzle 104 arranged in the inlet 14 of the container 4. The nozzle 4 is adapted for being rotated around an axis in parallel with an axis of the inlet 14 for conveying the gas along a helical path inside of the container 4. The nozzle 104 comprises an end portion facing the container inner chamber 12 having radially external surfaces defining a generally circular cross section shape that is matched to a dimension of an inner surface of the inlet 14. Further, the nozzle 104 comprises peripheral through-going channels adapted for creating a helical flow inside of the container 4.

The ionization device 102 further comprises a first fluid flow directing unit 106 arranged in the container 4. The first fluid flow directing unit 106 is arranged downstream of the first pair 18 of electrodes. More specifically, the first fluid flow directing unit 106 is arranged downstream of the second pair 44 of electrodes.

The first fluid flow directing unit 106 is adapted to compensate for a pressure drop throughout the length of the container 4 by providing a hindrance to the gas flow. In this way, a second arc structure created by the second pair 44 of electrodes may be as strong and disciplined as the first arc structure created by the first pair 18 of electrodes. More specifically, the pressure in the container 4 is maintained or at least not significantly reduced thanks to the first fluid flow directing unit 106. A distance between the molecules is decreased and the retention time in the container is increased and consequently the ionization efficiency increases. Further, maintaining the pressure at a relatively high level may be important for the delivery of the fluid to the tank 56, since the liquid in the tank provides a counterpressure that needs to be overcome.

Figure 6:
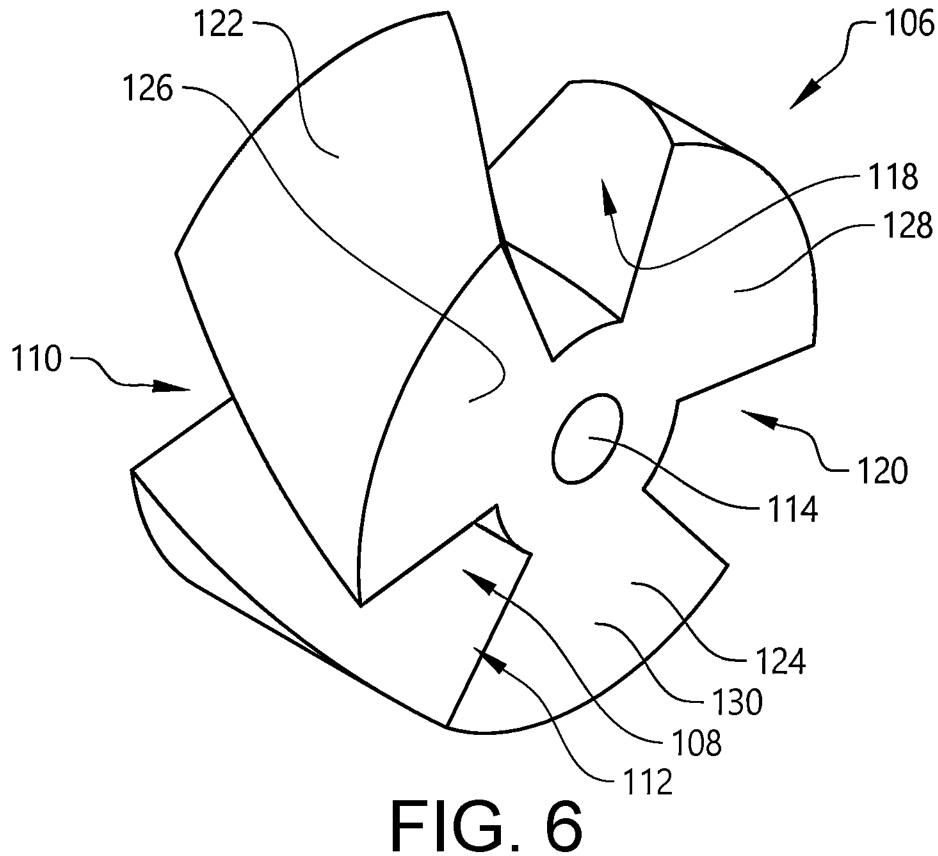
FIG. 6 is a perspective view of a fluid flow directing unit provided in the container in FIG. 6.
Figure 7:
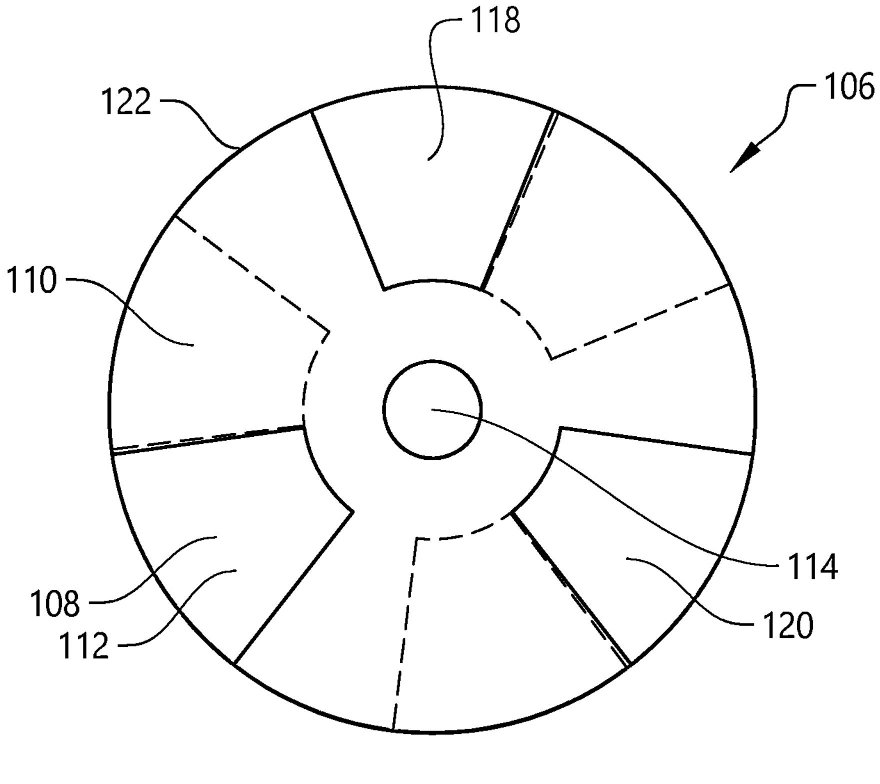
FIG. 7 is a front view of the fluid flow directing unit in FIG. 6.

FIG. 6 is a perspective view of the first fluid flow directing unit 106 provided in the container 4 in FIG. 1. FIG. 7 is a front view of the first fluid flow directing unit 106 in FIG. 6. The first fluid flow directing unit 106 comprises at least one peripheral fluid flow guide channel 108 having an outlet 110 circumferentially displaced relative to an inlet 112 for rotating a first portion of an incoming fluid flow. The first fluid flow directing unit 106 further comprises a central fluid flow guide channel 114 to an extension substantially in parallel with the longitudinal direction of the elongated container 4 for guiding a second portion of the incoming fluid flow substantially in the longitudinal direction of the elongated container 4.

More specifically, the first fluid flow directing unit 106 comprises a plurality of circumferentially spaced peripheral fluid flow guide channels 108, 118, 120. Further, the at least one peripheral fluid flow guide channel 108, 118, 120 has a substantially larger dimension than the central fluid flow guide channel 114 for conveying a substantially larger portion of the incoming fluid flow.

Further, the first fluid flow directing unit 106 has a rounded peripheral surface 122 substantially corresponding to a curvature of the rounded inner surface of the container 4, wherein the first fluid flow directing unit 106 is arranged in the container 4 so that the rounded surfaces are in contact with each other in a fluid tight manner.

More specifically, the first fluid flow directing unit 106 is rigidly connected, such as via weld seams, to the container 4 in an operational position. The first fluid flow directing unit

106 may be formed of a material with the same or similar expansion coefficient as the container wall 10. According to one example, the first fluid flow directing unit 106 is formed of glass. It creates conditions for rigidly connecting the first fluid flow directing unit 106 to the container 4 in the operational position via welding.

More specifically, the first fluid flow directing unit 106 comprises a body 124 defining the at least one peripheral fluid flow guide channel 108, 118, 120 and the central fluid flow guide channel 114. More specifically, the first fluid flow directing unit 106 is formed as a one-piece body 124.

The at least one peripheral fluid flow guide channel 108, 118, 120 is open in a radial direction of the first fluid flow directing unit 106. More specifically, at least one peripheral fluid flow guide channel 108, 118, 120 is closed in the radial direction by the wall 10 of the container 4 in FIG. 6.

The first fluid flow directing unit 106 comprises sections 126, 128, 130 circumferentially between adjacent peripheral fluid flow guide channels 108, 118, 120. A radially outer surface of these sections 126, 128, 130 of the first fluid flow directing unit 106 defines a circular shape of substantially the same dimension as the inner surface of the elongated container 4. A wall of each one of the sections 126, 128, 130 faces in the longitudinal direction of the container 4 for blocking parts of the fluid flow. A total area of the walls of the sections 126, 128, 130 is substantially the same as a cross section area defined by the peripheral fluid flow guide channels 108, 118, 120.

The first fluid flow directing unit 106 is adapted for conveying at least a first portion of the fluid along a helical path inside of the container 4 via the at least one peripheral fluid flow guide channel 108, 118, 120. Further, the first fluid flow directing unit 106 is adapted for conveying at least a second portion of the fluid along a substantially straight path inside of the container via the central fluid flow guide channel 114.

Figure 8:
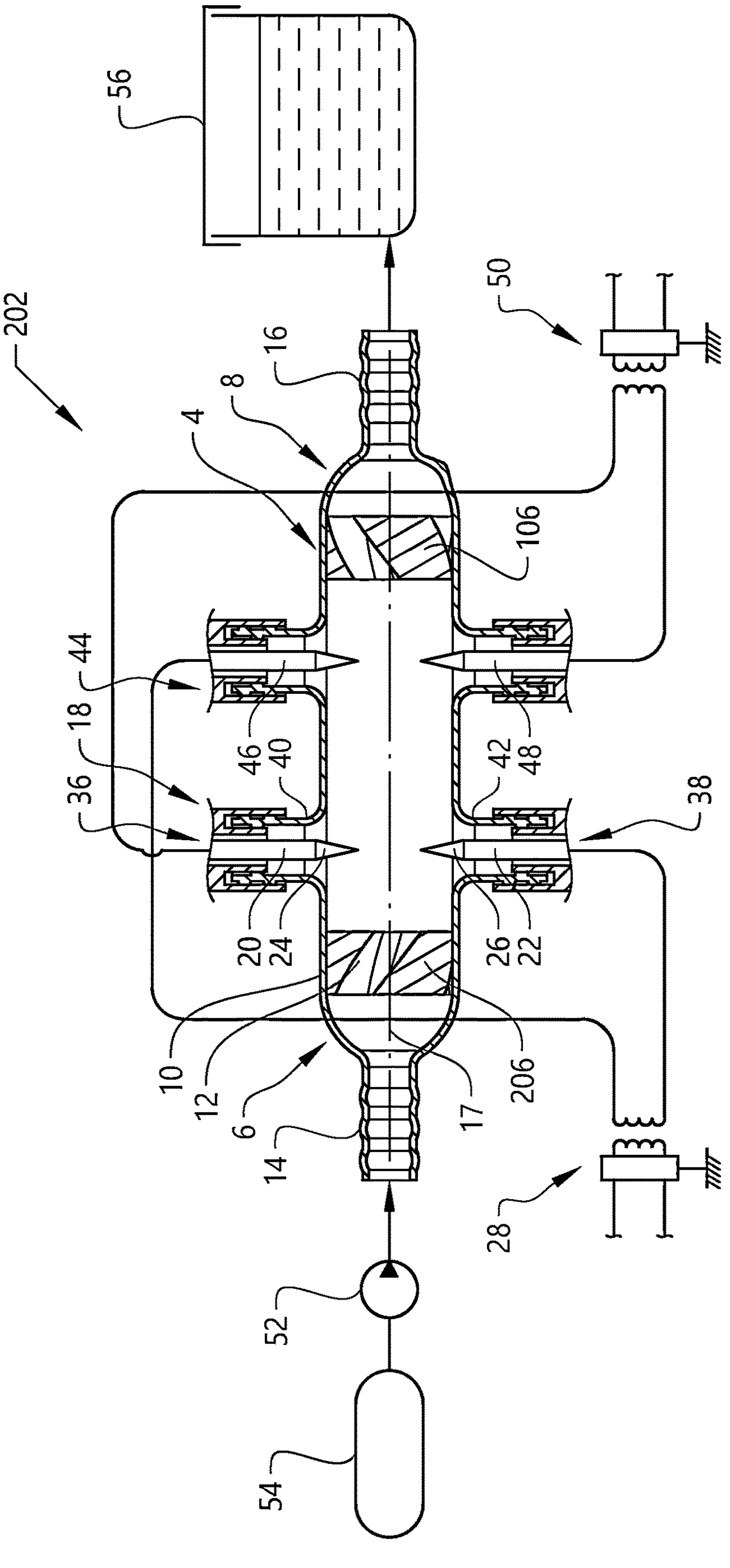
FIG. 8 is a schematic view of a device for ionization of a fluid according to a second embodiment, wherein a container is shown in a cross section.

FIG. 8 is a perspective view of a device 202 for ionization of a gas according to a second embodiment. The ionization device 202 according to the second embodiment has many parts in common with the ionization device 102 according to the first embodiment. For ease of presentation, only the main differences will be explained below.

The ionization device 202 comprises a second fluid flow directing unit 206. The two fluid flow directing units 106, 206 are arranged spaced from each other in the longitudinal direction of the container 4. More specifically, the two fluid flow directing units 106, 206 are arranged on opposite sides of the first pair 18 of electrodes 20, 22. More specifically, the two fluid flow directing units 106, 206 are arranged on opposite sides of the first pair 18 of electrodes 20, 22 and the second pair 44 of electrodes 46, 48. More specifically, the second fluid flow directing unit 206 has a design similar to the design of the first fluid flow directing unit 106 with the difference that the at least one peripheral fluid flow guide channel is rotated circumferentially in an opposite direction. Thus, the two fluid flow directing units 106, 206 are identical in dimension but have a mirrored design for the change of direction of the fluid flow. In other words, a first one of the two fluid flow directing units 106, 206 is adapted to rotate the fluid flow in a clockwise direction and the other one is adapted to rotate the fluid flow in a counter clockwise direction.

Figure 9:
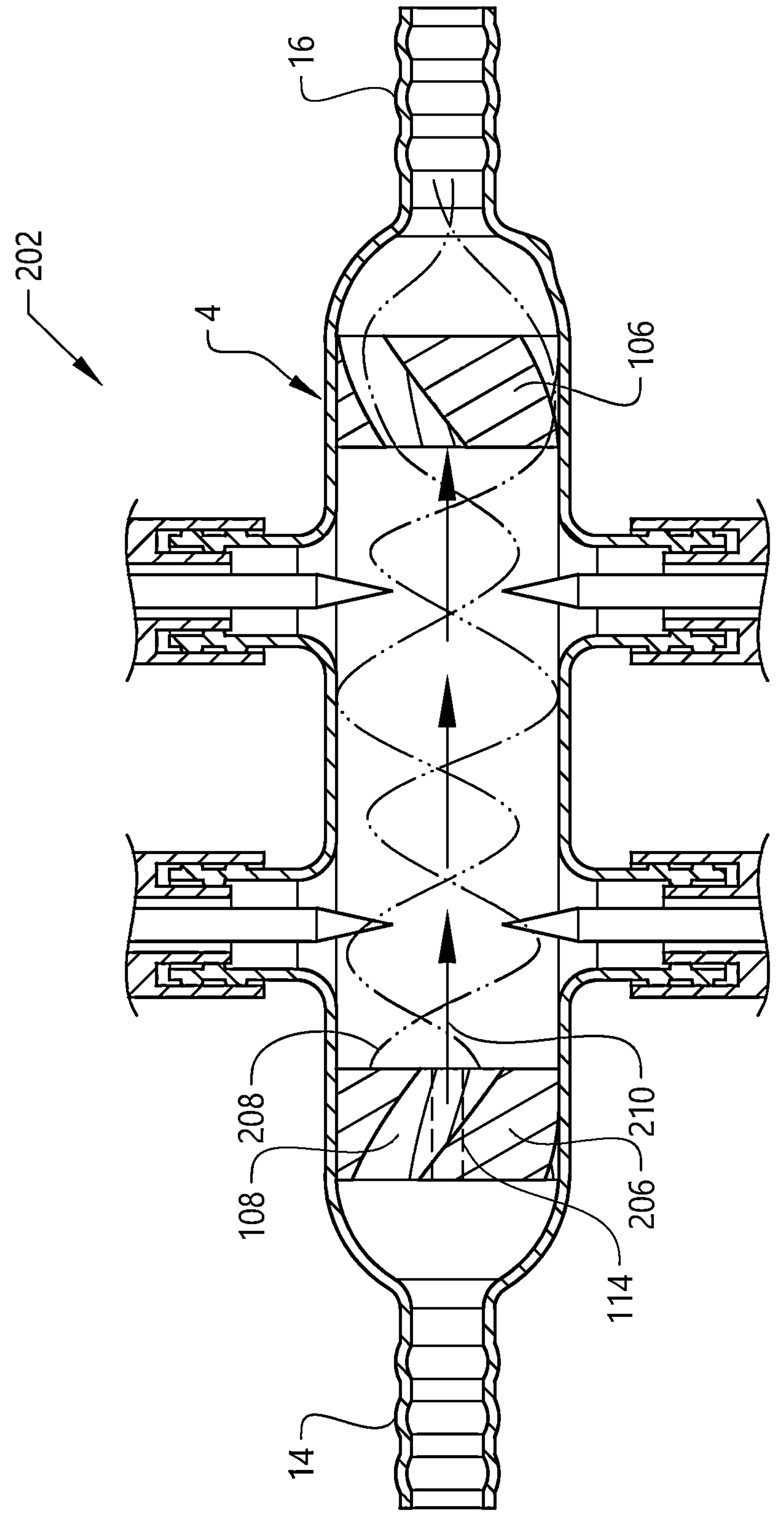
FIG. 9 is a cross section view of the container as in FIG. 8 indicating the fluid flow.

FIG. 9 is a schematic top view of the ionization device 202 as in FIG. 8 indicating the fluid flow paths. The peripheral fluid flow guide channels 108, 118, 120 of the upstream first fluid flow directing unit 206 are adapted to convey a first portion of the fluid flow in a helical path 208 inside the container 4. Further, the central fluid flow guide channel 114 is adapted to convey a second portion of the fluid flow in a substantially straight path 210 inside of the container in parallel to the longitudinal direction of the container 4.

Figure 10:
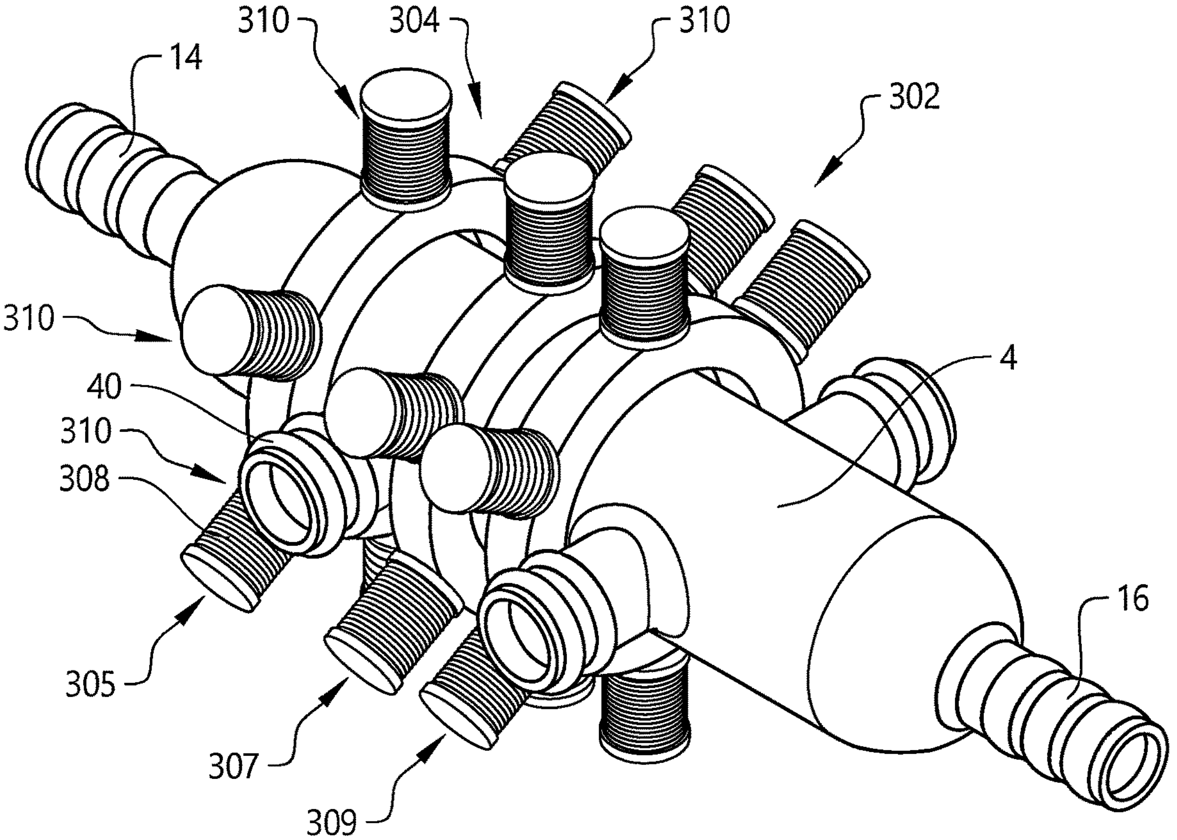
FIG. 10 is a perspective view of a device for ionization of a fluid according to a third embodiment.

FIG. 10 is a perspective view of parts of a device 302 for ionization of a gas according to a third embodiment. The ionization device 302 according to the third embodiment has many parts in common with the ionization device 202 according to the second embodiment. For ease of presentation, only the main differences will be explained below.

The ionization device 302 comprises a magnetic field generating arrangement 304, which is adapted for generating a magnetic field in the vicinity of the first pair 18 of electrodes for affecting the arc structures for supporting the ionization of the gas. The magnetic field generating arrangement 304 is arranged outside of the container 4. It creates conditions for a long life of the magnetic field generating arrangement 304 since it will not be subjected to the interior environment (friction and heat) of the container 4.

Figure 14:
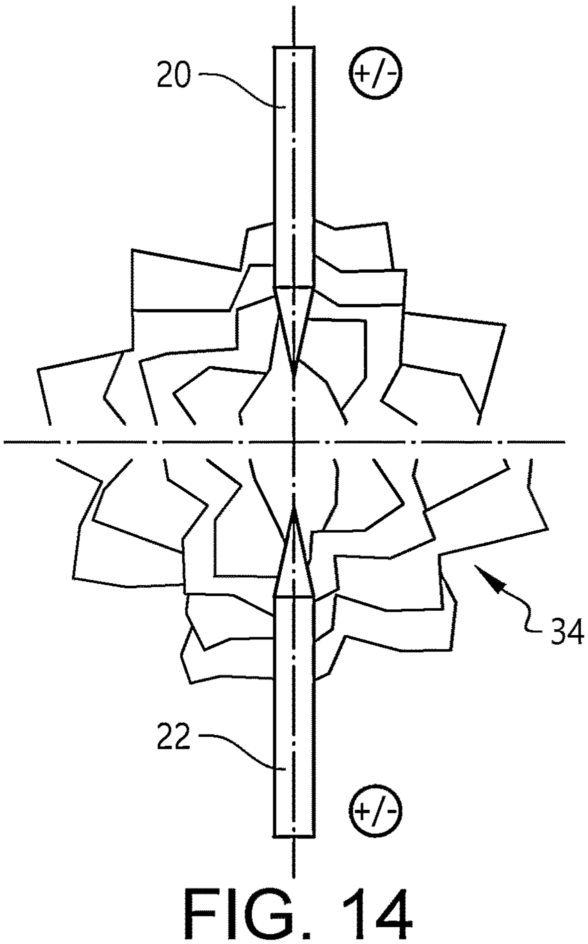
FIG. 14 is a schematic front view of the arc structures created in the container according to FIG. 10 by the first pair of electrodes.
Figure 15:
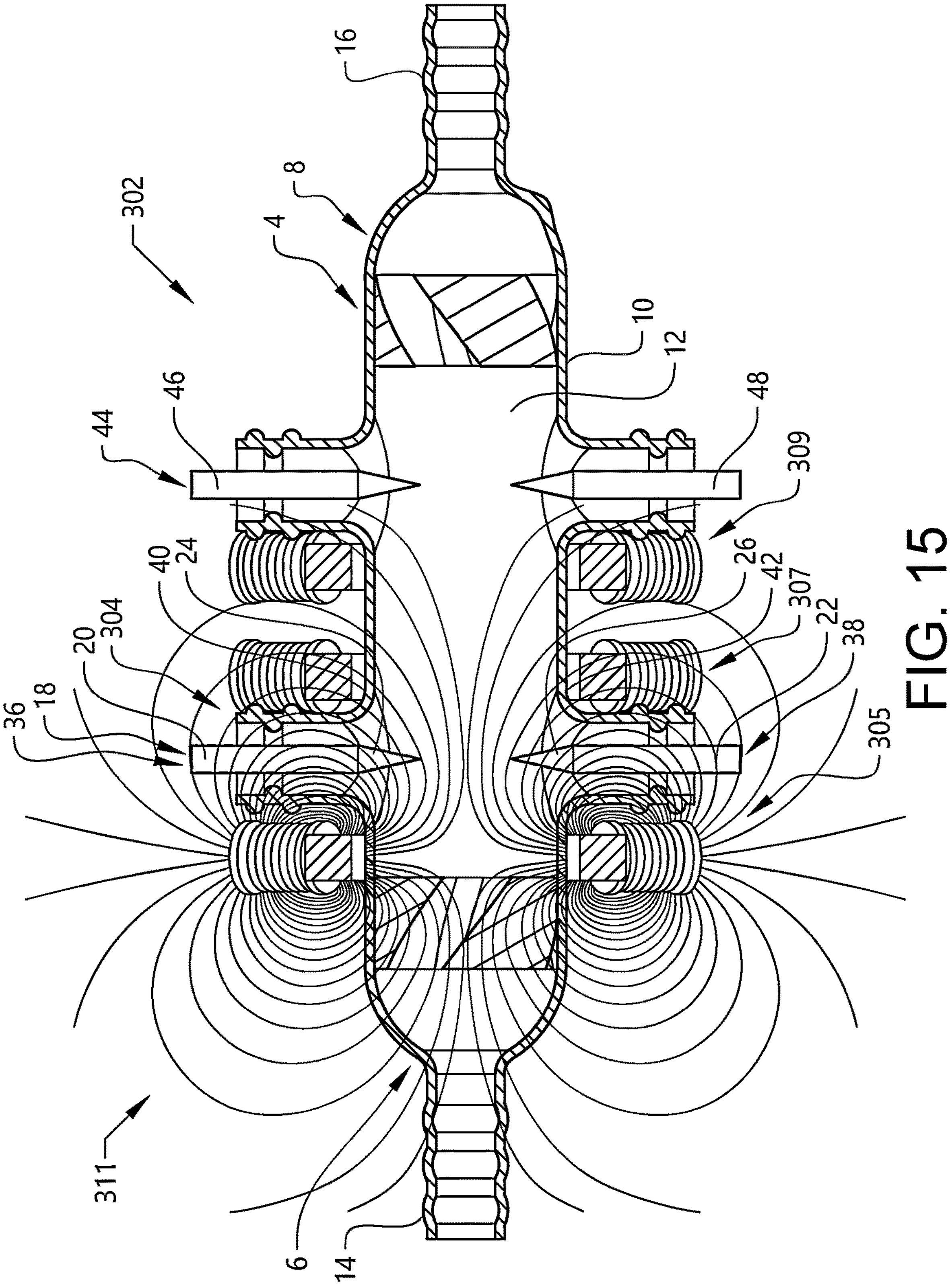
FIG. 15 is a schematic view in cross section of the container in FIG. 10 showing parts of the magnetic field generated by the magnetic field generating arrangement.

The magnetic field generating arrangement 304 comprises a first section 305 arranged upstream of the first pair 18 of electrodes in the longitudinal direction of the container, wherein the first arc structure 34 comprises a first set of arcs 334 that are deflected downstream from the electrodes by the gas flow and a second set of arcs 336 extending upstream from the electrodes 20, 22 by the effect of the magnetic field of the first magnetic field generating section 305. The first set of arcs 334 and the second set of arcs 336 are shown in FIG. 14 and FIG. 15. It should be noted that the second set of arcs 336 comprises fewer arcs than the first set of arcs 334 and that the arcs in the second set of arcs 336 have a smaller extension in the longitudinal direction of the container relative to the first set of arcs 334.

More specifically, the magnetic field generated by the first magnetic field generating section 305 creates bridges/pathways for arcs also upstream of the electrode pair 18, see arrows 330 and 331 indicating the electrons emitted from the electrodes 20, 22. The second set of arcs 336 comprises a plurality of arcs between the electrodes 20, 22. Further, the magnetic field generated by the first magnetic field generating section 305 is adapted for deflecting the second set of arcs 336 upstream from the electrodes 20, 22 in a direction of the gas flow. Further, the arcs have a zigzag/saw-tooth shape.

The magnetic field generating arrangement 304 comprises at least one magnetic field generating unit 310. The magnetic field generating unit 310 is formed by an electromagnet 308. The electromagnet 308 comprises a coil adapted for the passage of electric current. The electromagnet 308 is arranged so that an axis of the coil extends in a radial direction in relation to the container 4. According to an alternative, the magnetic field generating unit 310 is formed by a permanent magnet. The magnetic field generating unit is adapted for providing a magnetic strength in a range of 20-180 and especially in a range of 20-40 N.

More specifically, the first magnetic field generating section 305 comprises a plurality of circumferentially spaced magnetic field generating units 310 around the container. According to the shown example, the first magnetic field generating section 305 comprises six circumferentially spaced magnetic field generating units 310 around the container. Such an arrangement provides for even more organized and symmetric arc structure spreading all around the electrode pair evenly in all direction and cover the whole cross-section of the reaction chamber. The number of magnetic field generating units 310 may of course be altered depending on the application. Further, each one of the circumferentially spaced magnetic field generating units 310 is formed by an electromagnet. The magnets may be connected to a low voltage circuit, for example 12 to 24 volts. According to an alternative, one or several or all of the circumferentially spaced magnetic field generating units 310 may be formed by a permanent magnet.

Figure 11:
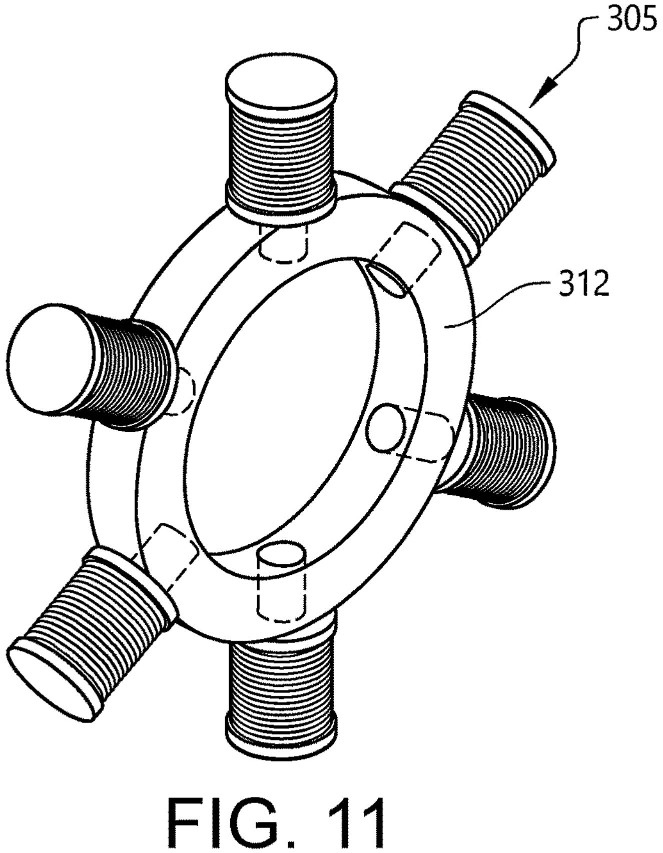
FIG. 11 is a perspective view of a section of a magnetic field generating arrangement provided around the container in FIG. 10.

Referring now also to FIG. 11 that is a perspective view of the first magnetic field generating section 305. The first magnetic field generating section 305 comprises a ring-shaped support 312 extending around the container, wherein the ring-shaped support is adapted to hold the circumferentially spaced magnetic field generating units 310 in their operational positions. Each one of the circumferentially spaced magnetic field generating units 310 is arranged so that its axis extends radially outwards from the ring-shaped support 312.

Figure 12:
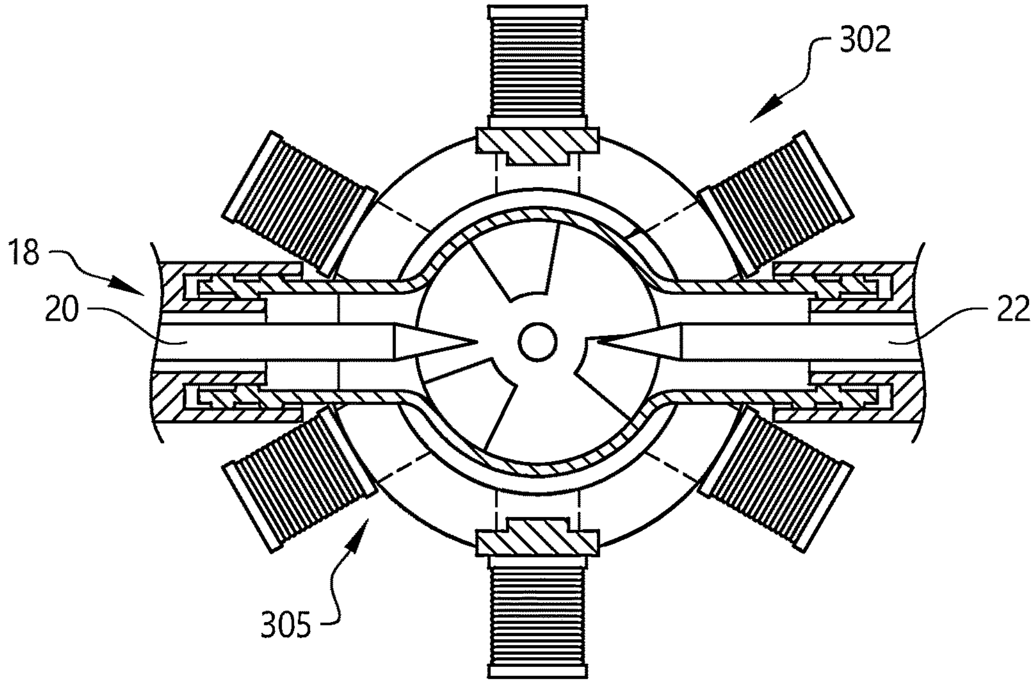
FIG. 12 is a schematic and partly cut front view of the magnetic field generating arrangement in FIG. 10.
Figure 13:
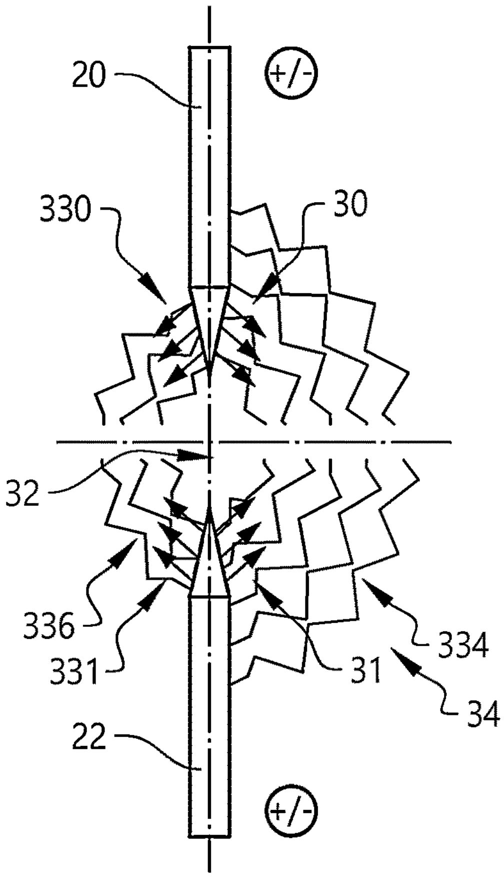
FIG. 13 is a schematic top view of arc structures created in the container according to FIG. 10 by the first pair of electrodes.

FIG. 12 is a partly cut front view of the ionization device 302 in FIG. 10. The ring-shaped support 312 is arranged in close proximity to an outer wall surface of the container 4. More specifically, the ring-shaped support 312 has an inner diameter that is substantially the same as or somewhat larger than an outer diameter of the container 4. It should be noted that the magnets are arranged so that a core of each magnet is in contact with an outer surface of the glass container. The ring-shaped support 312 is made of graphite or any non-conductive material with high thermal tolerance.

With reference to FIG. 10, the magnetic field generating arrangement 304 comprises a second section 307, which is arranged outside of the container and downstream of the first pair 18 of electrodes, in the longitudinal direction of the container 4, wherein the second magnetic field generating section 307 is adapted for generating a magnetic field in the vicinity of the first pair of electrodes for stabilizing the first arc structure. More specifically, the magnetic field created by the second magnetic field generating section 307 is adapted for disciplining the first set of arcs and give them a more coherent arrangement. In other words, the disciplining of the arcs means that the arcs form a more symmetric pattern with certain spacings etc. Also, the magnetic field created by the second magnetic field generating section 307 effects the first set of arcs to increase the quantity of the arcs as well as an increased thickness of the arcs. The second magnetic field generating section 307 is similar in construction and functionality as the first magnetic field generating section 305.

Further, the magnetic field generating arrangement 304 comprises a third section 309, which is arranged outside of the container and upstream of the second pair 44 of electrodes in the longitudinal direction of the container 4. The third magnetic field generating section 309 is adapted for generating a magnetic field in the vicinity of the second pair 44 of electrodes, similar to how the first magnetic field generating section 305 is adapted for generating the magnetic field in the vicinity of the first pair 18 of electrodes and will therefore not be described in any further detail here.

FIG. 15 is a schematic top view of the magnetic field generating arrangement 304 schematically showing parts 311 of the magnetic fields generated. More specifically, FIG. 15 shows the magnetic fields generated by two opposite magnetic field generating units 310. Similar magnetic fields are created by each one of the other two pairs of opposite magnetic field generating units 310.

Figure 16:
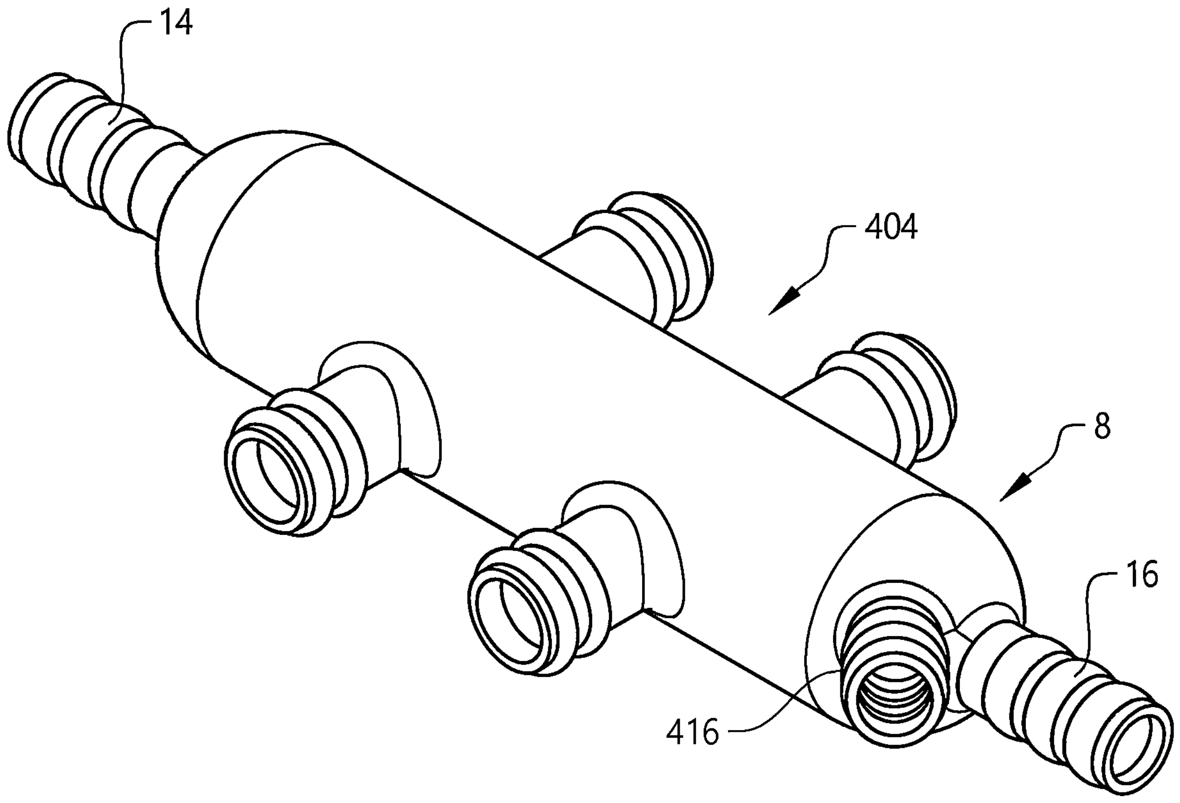
FIG. 16 is a perspective view of a container according to an alternative design relative to the container in FIG. 2.

FIG. 16 is a perspective view of a container 404 according to an alternative design relative to the container 4 in FIG. 2. The container 404 differs in relation to the container 4 in FIG. 2 in that it has a further outlet 416. The further outlet 416 is arranged inclined in relation to the longitudinal direction of the container 404. More specifically, the further outlet 416 is arranged with an angle of its axis in relation to the axis of the outlet 16 in a range of 30-60° and preferably about 45°. Further, the further outlet 416 is arranged extending from the half-spherical end 8 of the container 404. The arrangement of two outlets 16, 416 creates conditions for dividing the ionized gas flow into two separate gas flows to different destinations. According to one example, one of the outlets 16, 416 may be in fluid communication with the inlet 14 for recirculation of a portion of the ionized fluid flow.

Figure 17:
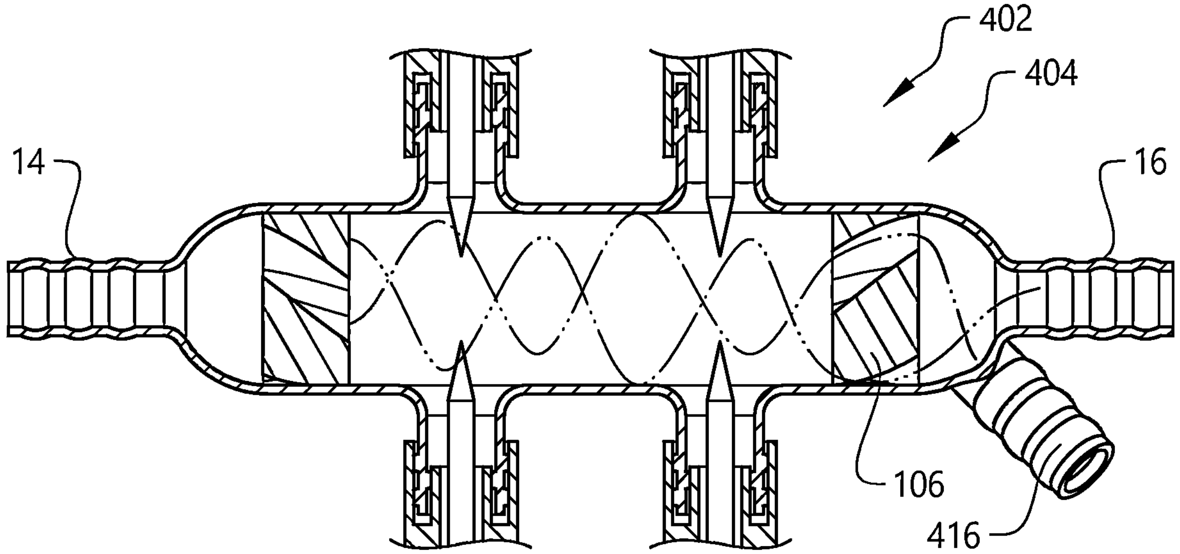
FIG. 17 is a schematic view of the container as in FIG. 16 in cross section applied in an ionization device according to a fourth embodiment indicating the fluid flow in operation.

FIG. 17 shows an ionization device 402 according to a fourth embodiment comprising the container 404 according to FIG. 16. It indicates the fluid flow paths inside of the container 404. More specifically, the design and position of the first fluid flow directing unit 106 is designed for conveying a first portion of the fluid towards the axial outlet 16 and a second portion of the fluid towards the further second outlet 416.

The ionization device 402 may as an alternative or complement to the first fluid flow directing unit 106 further comprise means for selective guiding of portions of the fluid flow to the outlets 16, 416. According to one example, the fluid flow selective guiding means is adapted to attract a negatively charged portion of the flow to the further outlet 416. It may be formed by a further electrode acting as a cathode. Since electrons has a negative charge and some of the ionized molecules/atoms are positively charged, the cathode may attract the negatively charged portion of the flow to the further outlet 416 and it can be used for another purpose (for example returning to the inlet 14 or for other purposes). In this way, the axial main output (the target ionization) in the axial outlet 16 is more purified. According to an alternative or complement, an anode may be used to absorb the positively charged portion of the flow depending on the purpose.

Figure 18:
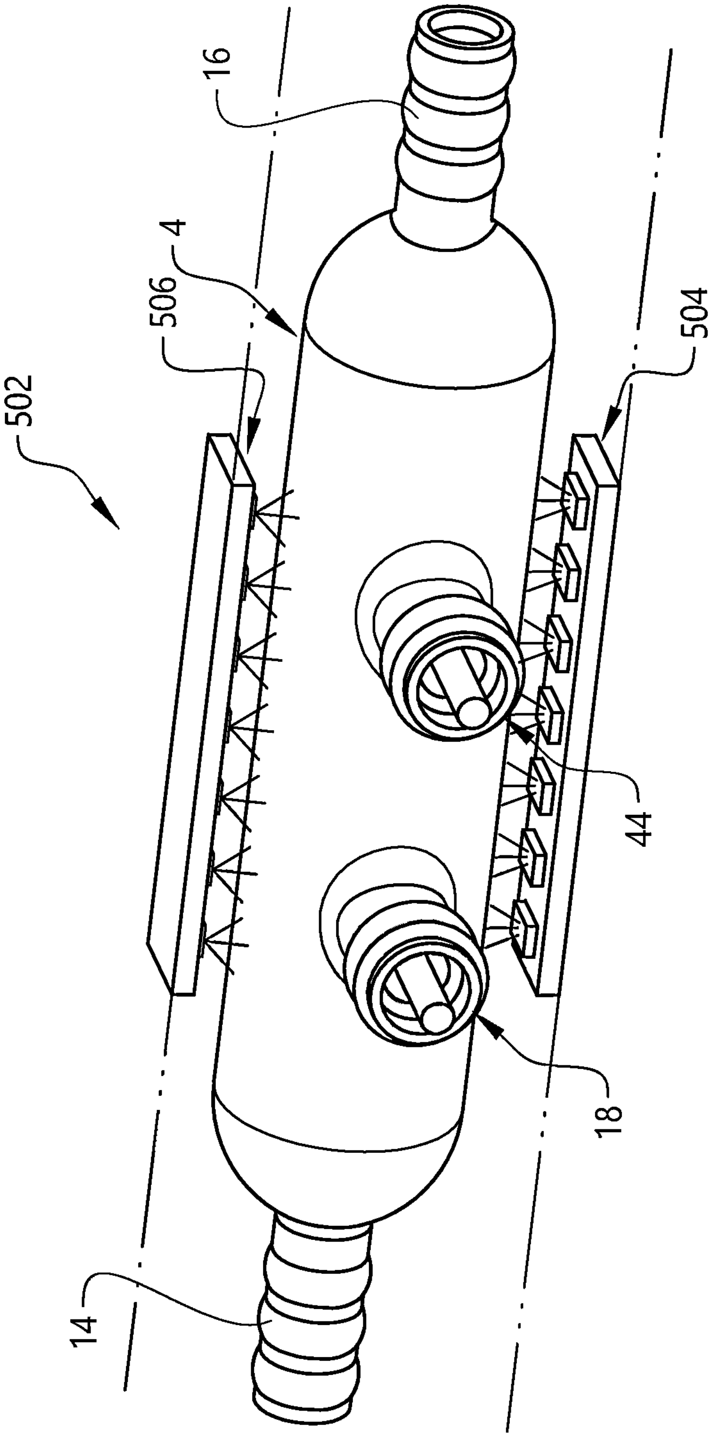
FIG. 18 is a perspective view of a device for ionization of a fluid according to a fifth embodiment.

FIG. 18 is a schematic side view of parts of an ionization device 502 according to a fifth embodiment. The ionization device 502 according to the fifth embodiment has many parts in common with the ionization device 102 according to the first embodiment. For ease of presentation, only the main differences will be explained below.

The ionization device 502 comprises at least one light source 504, 506, which is adapted to subject the gas flow in the container for radiation and thereby support the ionization of the gas. The light-matter interaction provides the phenomenon of pair production.

The light source 504, 506 is in the shape of a strip extending in the longitudinal direction of the container 4. The light source 504, 506 strip has a main extension along a straight line. More specifically, two light sources 504, 506 are arranged opposite each other, i.e., spaced to 180°. More specifically, the two light sources 504, 506 are arranged so that their longitudinal directions are in parallel with each other. More specifically, the strip shaped light source extends along a substantial part of the container 4 and in the shown example substantially along its complete length. The light source 504, 506 is arranged outside of the container 4. It creates conditions for a long life of the light source 504 since it will not be subjected to the interior environment (friction and heat) of the container 4. The radiation by the light source 504 may radiate the fluid flow due to the fact that the container wall is transparent.

The at least one light source 504, 506 comprises a plurality of light source units arranged in a spaced relationship in a longitudinal direction of the respective strip. The light source 504, 506 may be light-emitting diodes (LED)

adapted for radiating an ultraviolet (UV) light. According to an alternative, a Xenon lamp may be used. According to one example, the light sources 504, 506 may be adapted to provide a light intensity in a range of 100-5600 Lumen. The light intensity may be matched to the magnitude of the voltage supplied to the electrodes, wherein a lower voltage may be compensated by a higher light intensity for a certain ionization effect.

According to an alternative, the light source may be a light bulb instead of a strip. Also other shapes and arrangements of the light source may be applicable.

Figure 19:
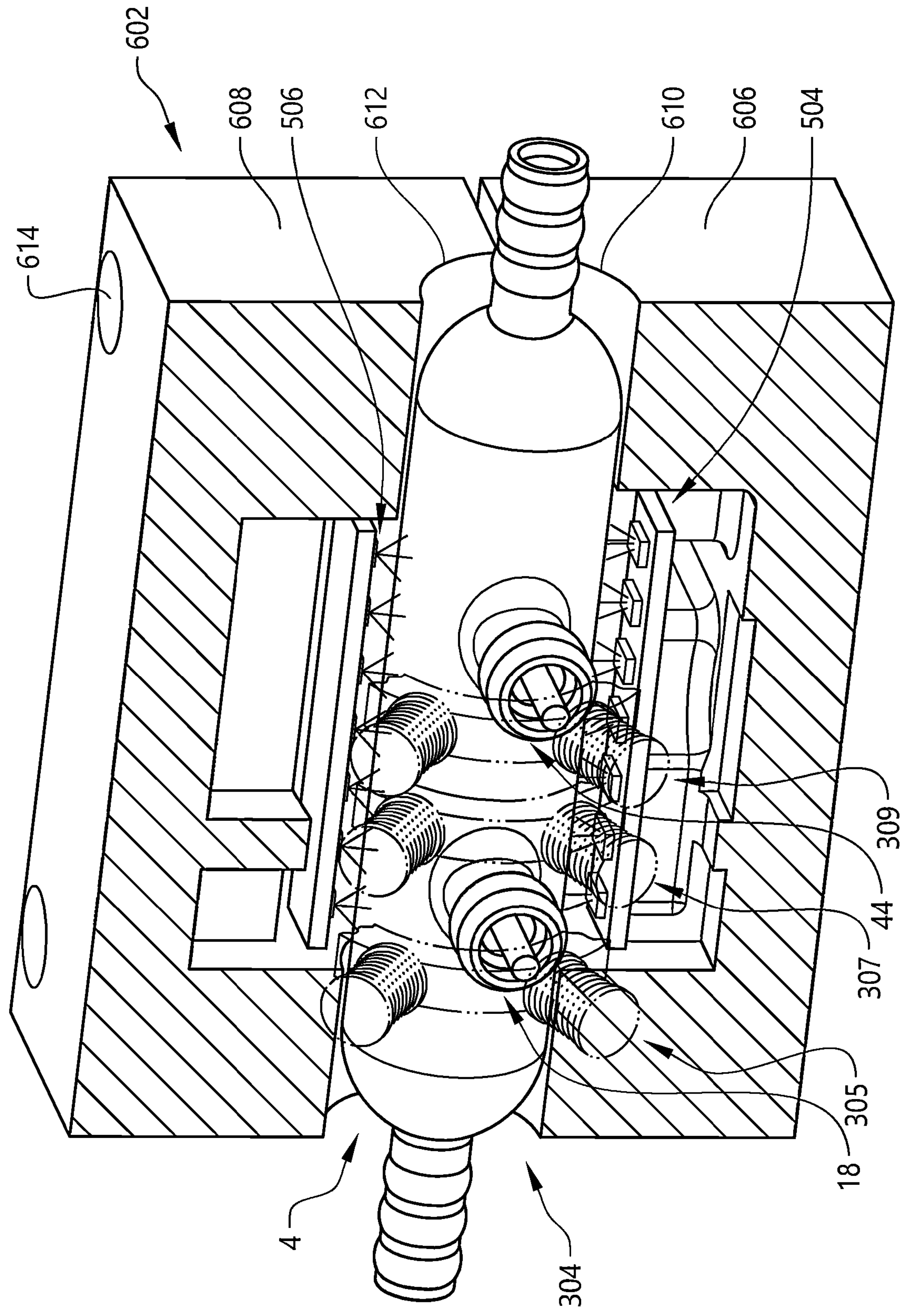
FIG. 19 is a perspective view of a device for ionization of a fluid according to a sixth embodiment.
Figure 20:
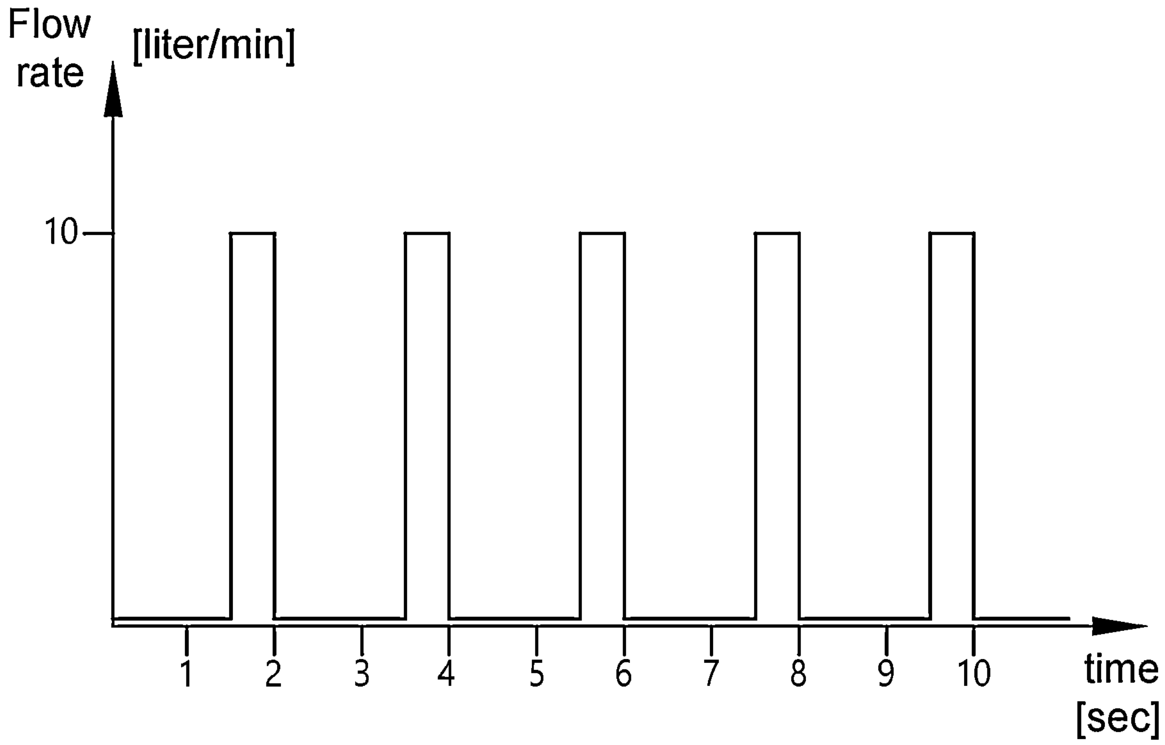
FIG. 20 is a graph indicating an example of a pulsed flow supplied to the ionization device.

FIG. 19 is a schematic and partly cut side view of parts of an ionization device 602 according to a sixth embodiment. The ionization device 602 according to the sixth embodiment has many parts in common with the ionization device 502 according to the fifth embodiment. For ease of presentation, only the main differences will be explained below.

The ionization device 602 comprises the magnetic field generating arrangement 304 as in FIG. 10. The ionization device 602 further comprises a support structure for supporting the container 4, the light sources 504, 506 and the magnetic field generating arrangement 304 in predefined positions. More specifically, the support structure comprises two blocks 606, 608. The blocks 606, 608 are adapted to be positioned on top of each other. Each block 606, 608 comprises a receptacle 610, 612 in the surfaces adapted to face each other. The receptacle 610, 612 has an elongated extension defining a half-circle in cross section for receiving the container 4. Further, each block 606, 608 is designed with internal chambers/receptacles for receiving the light sources 504, 506 and the magnetic field generating arrangement 304. Further, each block 606, 608 is provided with through holes 614 in a certain configuration for matching each other in order to receive bolts for securing the blocks 606, 608 to each other. Further, each block 606, 608 may be adapted to also receive the transformers 28, 50.

Figure 21:
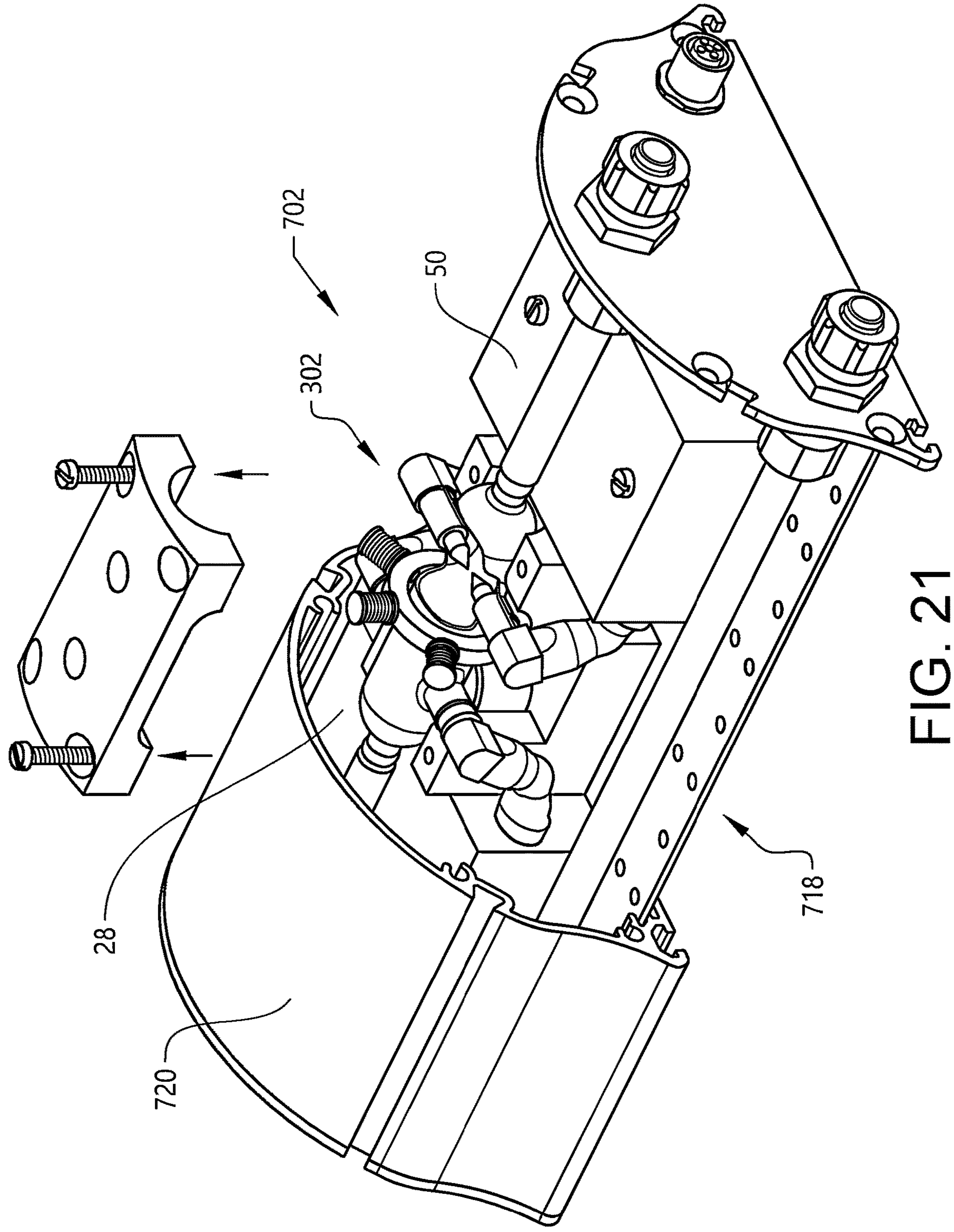
FIG. 21 is a partly cut and exploded perspective view of an arrangement for ionization of a fluid.

FIG. 21 is a partly cut and exploded perspective view of an arrangement 702 for ionization of a fluid. The arrangement 702 comprises the ionization device 302 in FIG. 11 arranged in a casing that has a generally circular cylindrical outer shape. The arrangement 702 comprises a generally flat rectangular wall 718 and wall 720 that is generally half-circular in cross section, which is connected to the flat rectangular wall 718 in a way defining an internal space between the walls 718, 720. The ionization device 302 is arranged in the internal space between the walls 718, 720. The transformers 28, 50 are arranged on either side of the container 4 in its longitudinal direction and connected to the electrodes 20, 22, 46, 48 as described above. Further, the transformers are located within the internal space between the walls 718, 720.

Figure 22:
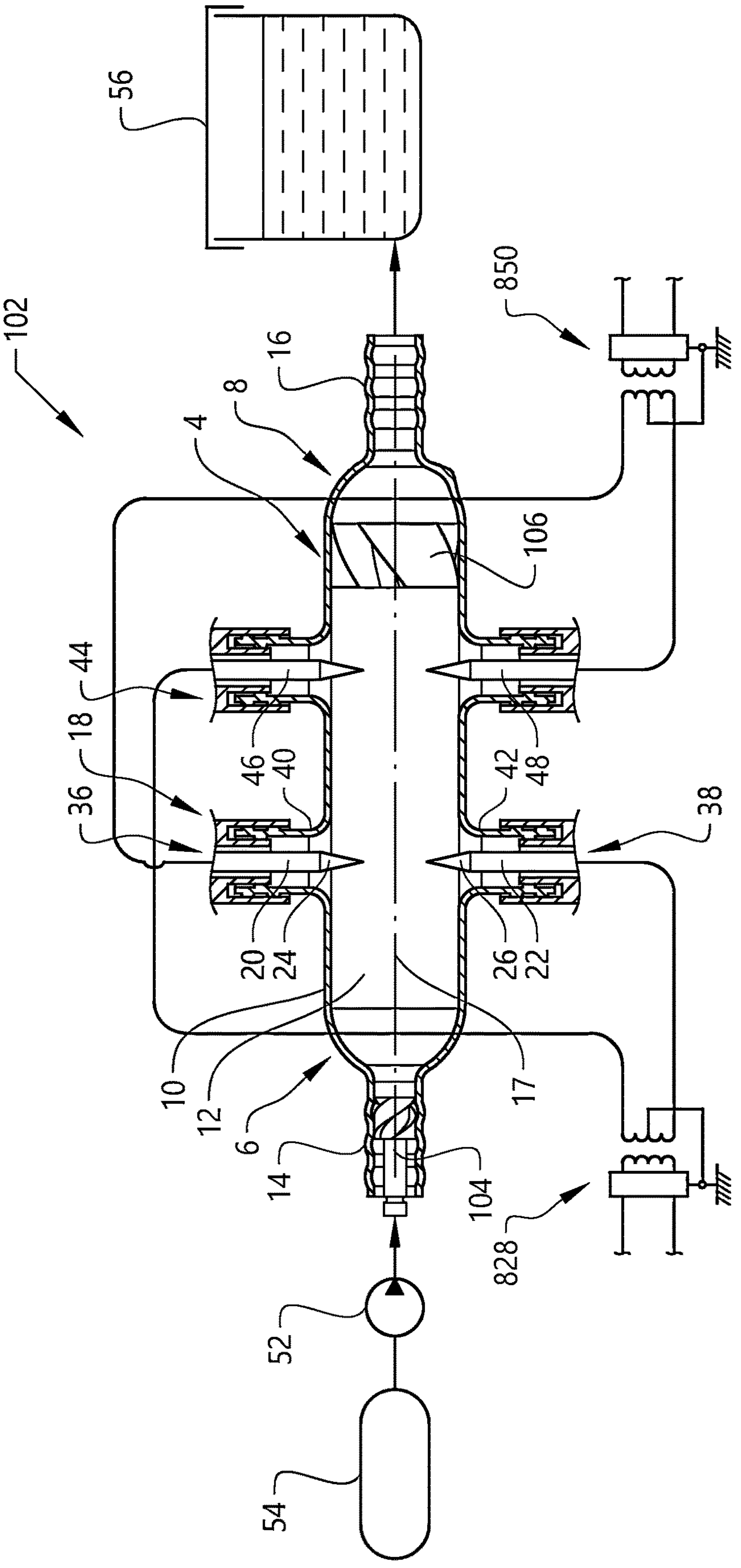
FIG. 22 is a schematic view of a device for ionization of a fluid according to an alternative to the first embodiment.

FIG. 22 is a schematic view of a device 802 for ionization of a fluid according to an alternative to the first embodiment. The ionization device 802 differs from the first embodiment in the structure of the transformers 828, 850. More specifically, a secondary mid-point of a secondary winding is connected to earth.

It is to be understood that the present invention is not limited to the embodiments described above and illustrated in the drawings; rather, the skilled person will recognize that many changes and modifications may be made within the scope of the appended claims.

The invention has been described above for an application of cleaning industrial process liquids. According to an alternative, the invention may be used for cleaning wastewater, such as municipal wastewater. According to an alternative, the invention may be used for cleaning air, such as air in buildings. The ionized gas may be used for eliminating organic and mineral impurities or pollutants. Such organic matter may be bacteria, viruses, other harmful microorganisms, and some organic chemical substances.

Further, the invention has been described for guiding a fluid flow with regard to embodiments where each one of the electrodes in the first pair of electrodes are charged so that they are simultaneously negatively or positively charged. In this way, a potential difference between each one of the electrodes and an environment of the respective electrode that electric discharges take place from each one of the electrodes simultaneously. Accordingly, a plurality of independent semi arc structures formed at the same time from each one of the electrodes in the first pair. Similarly for the second pair of electrodes, they are charged so that electric discharges take place from each one of the electrodes. According to an alternative embodiment, the guiding of the fluid flow may be used for a device where a first one of the electrodes in one pair is positively charged and a second one of the electrodes in the same pair is negatively charged, wherein continuous arc structures may be realized extending between the electrodes in each pair.

The invention claimed is:

1. A device for ionization of a fluid, wherein the device comprises:

an elongated container adapted for conveying the fluid in a gaseous state, a fluid ionizing arrangement for ionizing the fluid, and at least one fluid flow directing unit arranged in the container, wherein the at least one fluid flow directing unit comprises at least one peripheral fluid flow guide channel having an outlet circumferentially displaced relative to an inlet for rotating a first portion of an incoming fluid flow, and a central fluid flow guide channel which extends substantially in parallel to the longitudinal direction of the elongated container for guiding a second portion of the incoming fluid flow substantially in the longitudinal direction of the elongated container, wherein an outlet of the at least one fluid flow directing unit is arranged within the elongated container at a distance from an outlet end of the elongated container.

2. The device according to claim 1, wherein the at least one fluid flow directing unit comprises a plurality of circumferentially spaced peripheral fluid flow guide channels.

3. The device according to claim 1, wherein the at least one peripheral fluid flow guide channel has a substantially larger dimension than the central fluid flow guide channel for conveying a substantially larger portion of the incoming fluid flow.

4. The device according to claim 1, wherein the container has a rounded inner surface and the at least one fluid flow directing unit has a rounded peripheral surface substantially corresponding to a curvature of the rounded inner surface of the container, wherein the at least one fluid flow directing unit is arranged in the container so that the rounded surfaces are in contact with each other.

5. The device according to claim 1, wherein the container and the at least one fluid flow directing unit are rigidly connected.

6. The device according to claim 1, wherein the at least one fluid flow directing unit comprises a body defining the at least one peripheral fluid flow guide channel and the central fluid flow guide channel.

7. The device according to claim 1, wherein an inner surface of the elongated fluid container has a circular shape in a cross section transverse to its longitudinal direction and a radially outer surface of the at least one fluid flow directing unit defines a circular shape of substantially the same dimension as the inner surface of the elongated fluid container.

8. The device according to claim 7, wherein the inner surface of the elongated fluid container has a diameter in a range of 10-50 mm.

9. The device according to claim 1, wherein the device comprises a first fluid flow directing unit and a second fluid flow directing unit adapted for directing at least a portion of the fluid flow in a helical path inside of the container and wherein the first fluid flow directing unit is arranged spaced from the second fluid flow directing unit downstream in the longitudinal direction of the container and arranged so that the at least one peripheral fluid flow guide channel deflects the fluid flow from the helical path.

10. The device according to claim 1, wherein the fluid ionizing arrangement comprises a first pair of electrodes arranged in the elongated container opposite each other and at a distance from each other in a transverse direction of the elongated container, wherein the container is adapted for conveying the fluid in the gaseous state in a fluid flow past the first pair of electrodes, and wherein the device further comprises a power supply adapted to charge the first pair of electrodes so that electric discharges takes place from the electrodes for ionization of the fluid.

11. The device according to claim 10, wherein one of the at least one fluid flow directing unit is arranged in the container upstream of the first pair of electrodes in a direction of the fluid flow, wherein the central fluid flow guide channel is adapted for guiding the second part portion of the incoming fluid flow towards a position between the electrodes in the first pair for deflecting the electric discharges downstream.

12. The device according to claim 10, wherein one of the at least one fluid flow directing unit is arranged in the container downstream of the first pair of electrodes in a direction of the fluid flow.

13. The device according to claim 10, wherein the power supply is adapted to charge the first pair of electrodes so that they are simultaneously negatively or positively charged for creating such a potential difference between each one of the electrodes and an environment of the respective electrode that electric discharges takes place from each one of the electrodes, and wherein the container is adapted for conveying the fluid in a gaseous state in a flow past the first pair of electrodes in the environment of the respective electrode during said charging for ionization of the fluid.

14. The device according to claim 13, wherein the device further comprises a second pair of electrodes arranged in the container opposite each other and at a distance from each other, wherein the second pair of electrodes are arranged at a distance from the first pair of electrodes downstream of the first pair in a fluid flow direction in the container, wherein the power supply is adapted to charge each one of the electrodes in the second pair of electrodes so that they are simultaneously negatively or positively charged and to synchronize the charging of the first pair of electrodes in relation to the second pair of electrodes so that the second pair of electrodes are negatively charged when the first pair of electrodes are positively charged and vice versa.

15. The device according to claim 13, wherein a first electrode in the first pair of electrodes and a first electrode in the second pair of electrodes are connected to opposite terminals of a first power supply and wherein a second electrode in the first pair of electrodes and a second electrode in the second pair of electrodes are connected to opposite terminals of a second power supply.

16. The device according to claim 10, wherein the device further comprises a magnetic field generating arrangement, which is adapted for generating a magnetic field in the vicinity of the first pair of electrodes for affecting a structure of the electric discharges for supporting the ionization of the fluid.

17. The device according to claim 10, wherein the electrodes are provided with chemical coatings adapted to increase the corrosion resistance of the electrodes.

18. The device according to claim 1, wherein the device comprises a fluid flow pumping means for supplying the fluid flow to an inlet of the container with a fluid flow rate in a range of 5-80 litre/min.

19. The device according to claim 1, wherein the device further comprises a fluid flow pumping means that is adapted for supplying the fluid flow in a pulsed manner to an inlet of the container.

20. The device according to claim 1, wherein the device is adapted to be operated with a pressure in the container above 1.1 bars.

21. The device according to claim 1, wherein the device further comprises a light source arranged for radiating the fluid in the container.

* * * * *